(12) United States Patent
Spurlin et al.

(10) Patent No.: US 7,737,581 B2
(45) Date of Patent: Jun. 15, 2010

(54) METHOD AND APPARATUS FOR PREDICTING END OF BATTERY LIFE

(75) Inventors: Jon Spurlin, Northridge, CA (US); John Gablenz, Centerville, MN (US); Kaezad J. Mehta, Chatsworth, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 624 days.

(21) Appl. No.: 11/447,637

(22) Filed: Jun. 6, 2006

(65) Prior Publication Data

US 2007/0040449 A1    Feb. 22, 2007

Related U.S. Application Data

(63) Continuation-in-part of application No. 11/204,667, filed on Aug. 16, 2005, and a continuation-in-part of application No. 11/204,583, filed on Aug. 16, 2005.

(51) Int. Cl.
*H02J 7/00* (2006.01)
*H02J 9/00* (2006.01)

(52) U.S. Cl. ......................................... 307/66
(58) Field of Classification Search .................... 307/66
See application file for complete search history.

(56) References Cited

U.S. PATENT DOCUMENTS

| 4,433,072 A | 2/1984 | Pusineri et al. |
| 4,494,950 A | 1/1985 | Fischell |
| 4,562,751 A | 1/1986 | Nason et al. |

(Continued)

FOREIGN PATENT DOCUMENTS

EP    0695017 A2    1/1996

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner*—Fritz M Fleming
*Assistant Examiner*—Dru M Parries
(74) *Attorney, Agent, or Firm*—Pillsbury Winthrop Shaw Pittman LLP

(57) ABSTRACT

A powering subassembly for a portable electronic device includes a main battery, a converter, a backup battery, and a controller. The main battery provides a main voltage and the backup battery can provide a backup voltage. The converter receives the main voltage and increases the main voltage to at least one operating voltage. The controller receives the operating voltage from the converter, monitors the voltage of the main battery, and compares the monitored main battery voltage to a main battery low voltage threshold. The controller transmits a disconnect signal to decouple the main battery from the converter if the monitored voltage from the main battery is less than the main battery low voltage threshold. The controller transmits a connection signal to couple the backup battery to the converter if the monitored voltage is less than the main battery low voltage threshold. The backup battery provides the power for a predetermined minimum amount of time.

37 Claims, 12 Drawing Sheets

U.S. PATENT DOCUMENTS

| | | | |
|---|---|---|---|
| 4,671,288 A | 6/1987 | Gough | |
| 4,678,408 A | 7/1987 | Nason et al. | |
| 4,685,903 A | 8/1987 | Cable et al. | |
| 4,731,726 A | 3/1988 | Allen, III | |
| 4,781,798 A | 11/1988 | Gough | |
| 4,871,351 A | 10/1989 | Feingold | |
| 4,908,523 A | 3/1990 | Snowden et al. | |
| 5,080,653 A | 1/1992 | Voss et al. | |
| 5,097,122 A | 3/1992 | Colman et al. | |
| 5,101,814 A | 4/1992 | Palti | |
| 5,108,819 A | 4/1992 | Heller et al. | |
| 5,165,407 A | 11/1992 | Wilson et al. | |
| 5,191,500 A * | 3/1993 | Hatano et al. | 361/64 |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,356,786 A | 10/1994 | Heller et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,497,772 A | 3/1996 | Schulman et al. | |
| 5,543,326 A | 8/1996 | Heller et al. | |
| 5,569,186 A | 10/1996 | Lord et al. | |
| 5,586,553 A | 12/1996 | Halili et al. | |
| 5,593,852 A | 1/1997 | Heller et al. | |
| 5,660,163 A | 8/1997 | Schulman et al. | |
| 5,665,065 A | 9/1997 | Colman et al. | |
| 5,665,222 A | 9/1997 | Heller et al. | |
| 5,684,384 A * | 11/1997 | Barkat et al. | 307/66 |
| 5,717,308 A | 2/1998 | Nishitani et al. | |
| 5,750,926 A | 5/1998 | Schulman et al. | |
| 5,779,665 A | 7/1998 | Mastrototaro et al. | |
| 5,791,344 A | 8/1998 | Schulman et al. | |
| 5,800,386 A | 9/1998 | Bellifemine | |
| 5,814,972 A | 9/1998 | Shimada et al. | |
| 5,835,366 A * | 11/1998 | Pleso et al. | 363/59 |
| 5,904,708 A | 5/1999 | Goedeke | |
| 5,917,346 A | 6/1999 | Gord et al. | |
| 5,965,380 A | 10/1999 | Heller et al. | |
| 5,972,199 A | 10/1999 | Heller et al. | |
| 5,999,848 A | 12/1999 | Gord et al. | |
| 5,999,849 A | 12/1999 | Gord et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,169,387 B1 * | 1/2001 | Kaib | 320/132 |
| 6,175,752 B1 | 1/2001 | Say et al. | |
| 6,259,937 B1 | 7/2001 | Schulman et al. | |
| 6,329,161 B1 | 12/2001 | Heller et al. | |
| 6,472,122 B1 | 10/2002 | Schulman et al. | |
| 6,475,750 B1 | 11/2002 | Han et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,554,798 B1 | 4/2003 | Mann et al. | |
| 6,558,320 B1 | 5/2003 | Causey, III et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,654,625 B1 | 11/2003 | Say et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,733,471 B1 | 5/2004 | Ericson et al. | |
| 6,746,582 B2 | 6/2004 | Heller et al. | |
| 6,749,740 B2 | 6/2004 | Liamos et al. | |
| 6,752,787 B1 | 6/2004 | Causey et al. | |
| 6,809,653 B1 | 10/2004 | Mann et al. | |
| 6,881,551 B2 | 4/2005 | Heller et al. | |
| 6,893,545 B2 | 5/2005 | Gotoh et al. | |
| 6,916,159 B2 | 7/2005 | Rush et al. | |
| 6,932,894 B2 | 8/2005 | Mao et al. | |
| 6,942,518 B2 | 9/2005 | Liamos et al. | |
| 6,945,934 B2 | 9/2005 | Bardy | |
| 2001/0022472 A1 * | 9/2001 | Codina et al. | 307/66 |
| 2002/0045808 A1 | 4/2002 | Ford et al. | |
| 2002/0058906 A1 | 5/2002 | Lebel et al. | |
| 2002/0065454 A1 | 5/2002 | Lebel et al. | |
| 2002/0082665 A1 | 6/2002 | Haller et al. | |
| 2002/0107476 A1 | 8/2002 | Mann et al. | |
| 2002/0151771 A1 * | 10/2002 | Braun et al. | 600/300 |
| 2002/0161288 A1 | 10/2002 | Shin et al. | |
| 2002/0169636 A1 | 11/2002 | Eggers et al. | |
| 2002/0198513 A1 | 12/2002 | Lebel et al. | |
| 2003/0078560 A1 | 4/2003 | Miller et al. | |
| 2003/0088166 A1 | 5/2003 | Say et al. | |
| 2003/0140929 A1 | 7/2003 | Wilkes et al. | |
| 2003/0152823 A1 | 8/2003 | Heller et al. | |
| 2003/0168338 A1 | 9/2003 | Gao et al. | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0212317 A1 | 11/2003 | Kovatchev et al. | |
| 2003/0212379 A1 | 11/2003 | Bylund et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2004/0143405 A1 * | 7/2004 | Tsai et al. | 702/63 |
| 2004/0193025 A1 | 9/2004 | Steil et al. | |
| 2004/0215492 A1 | 10/2004 | Choi | |
| 2004/0235446 A1 * | 11/2004 | Flaherty et al. | 455/352 |
| 2005/0038332 A1 | 2/2005 | Saidara et al. | |
| 2005/0059895 A1 | 3/2005 | Brown | |
| 2005/0065464 A1 | 3/2005 | Talbot et al. | |
| 2005/0137530 A1 | 6/2005 | Campbell et al. | |
| 2005/0137573 A1 | 6/2005 | McLaughlin | |
| 2005/0143635 A1 | 6/2005 | Kamath et al. | |
| 2005/0154271 A1 | 7/2005 | Rasdal et al. | |
| 2005/0182308 A1 | 8/2005 | Bardy | |
| 2005/0197553 A1 | 9/2005 | Cooper | |

| | | |
|---|---|---|
| 2005/0214585 A1 | 9/2005 | Li et al. |
| 2005/0239156 A1 | 10/2005 | Drucker et al. |
| 2006/0025663 A1 | 2/2006 | Talbot et al. |
| 2006/0058627 A1 | 3/2006 | Flaherty et al. |
| 2006/0173260 A1 | 8/2006 | Gaoni et al. |
| 2006/0182658 A1 | 8/2006 | Wu et al. |
| 2006/0259676 A1 | 11/2006 | Oberding et al. |
| 2006/0261781 A1 | 11/2006 | Oberding et al. |
| 2007/0004969 A1 | 1/2007 | Kong et al. |
| 2007/0093786 A1 | 4/2007 | Goldsmith et al. |
| 2008/0200897 A1 | 8/2008 | Hoss et al. |

FOREIGN PATENT DOCUMENTS

| | | |
|---|---|---|
| EP | 1338295 | 8/2003 |
| GB | 2 395 373 A | 5/2004 |
| JP | 11-149420 | 2/1999 |
| WO | WO 91/04601 | 4/1991 |
| WO | WO 96/37246 A1 | 11/1996 |
| WO | WO 01/08551 A2 | 2/2001 |
| WO | WO 02/058537 A2 | 8/2002 |

OTHER PUBLICATIONS

Abel et al., "A Method for Evaluating in vivo the Functional Characteristics of Glucose Sensors," Biosensors, 1986, pp. 211-220, vol. 2.
Boguslavsky et al., "Applications of redox polymers in biosensors," Solid State Ionics, 1993, pp. 189-197, vol. 60.
Geise et al., "Electropolymerized 1,3-diaminobenzene for the construction of a 1-1'-dimethylferrocene mediated glucose biosensor,"Analytica Chim. Acta.,1993, pp. 467-473, v18.
Gernet et al., "A planar glucose enzyme electrode," Sensors and Actuators, 1989, pp. 537-540, vol. 17, Elsevier Sequoia, Netherlands.
Gernet et al., "Fabrication and Characterization of a Planar Electrochemical Cell and Its Applications as a Glucose Sensor," Sensors and Actuators, 1989, pp. 49-70, vol. 18.
Gorton et al., "Amperometric glucose senosrs based on immobilized glucose-oxidizing enzymes and chemically modified electrodes," Analytica Chim Acta., 1991, pp. 43-54, v. 249.
Gorton et al., "Amperometric biosensors based on an apparent direct electron transfer between electrodes and immobilized peroxidases," Analyst, 1992, pp. 1235-1241, vol. 117.
Gough et al., "Two-Dimensional Enzyme Electrode Sensor for Glucose," Analytical Chemistry, 1985, pp. 2351-2357, vol. 57.
Gregg et al., "Redox polymer films containing enzymes," J. Phys. Chem., 1991, pp. 5970-5975.
Gregg et al., "Cross-Linked Redox Gels Containing Glucose Oxidase for Amperometric Biosensor Applications," Anal. Chem., 1990, pp. 258-263, vol. 62.
Heller et al., "Electrical Wiring of Redox Enzymes," Accounts of Chemical Research, 1990, pp. 128-134, vol. 23, No. 5.
Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," Electroanalysts, 1989, pp. 465-468, v.1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivio Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
Mastrototaro et al., "An Electroenzymatic Sensor Capable of 72 Hour Continuous Monitoring of Subcutaneous Glucose," 14th Int'l Diabetes Federation Congress, 1991.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors,"ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.
Nakamado et al., "A Lift-Off Method for Patterning Enzyme-Immobilized Membranes in Multi-Biosensors," Sensors and Actuators, 1988, pp. 165-172, vol. 13.
Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancrease—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.
Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That Can Be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.
Nishida et al., "Development of a ferrocene-mediated needle-type glucose sensor . . . ," Medical Process Through Technology, 1995, pp. 91-103, vol. 21.
Koudelka et al., "Planar Amperometric Enzyme-Based Glucose Microelectrode," Sensors and Actuators, 1989, pp. 157-165, vol. 18.
Yamasaki et al., "Direct measurement of whole blood glucose by a needle-type sensor," Clinica Chimica Acta., 1989, pp. 93-98, vol. 93.
Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-3179, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n.10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-2077, vol. 65.

Bindra et al., "Design and In Vitro Studies of a Needle-Type Glucose Sensor for Subcutaneous Monitoring," Anal. Chem., 1991, pp. 1692-1696, vol. 63.

"Battery Bank Switching", Jim T. Wiggenhorn, Motorola Technical Developments, 10, p. 18, Mar. 1990.

PCT International Search Report, May 26, 2008 (PCT/US2007/013249) (7 pages).

International Search Report and Written Opinion of the International Searching Authority, (PCT/US2009/068417) (Apr. 14, 2010) (14-pgs).

* cited by examiner

Electronics architecture utilizing custom IC.

METHOD AND APPARATUS FOR PREDICTING END OF BATTERY LIFE

CROSS-REFERENCE TO RELATED APPLICATIONS

This is a continuation-in-part of U.S. patent application Ser. No. 11/204,667, filed Aug. 16, 2005, and U.S. patent application Ser. No. 11/204,583, filed Aug. 16, 2005.

BACKGROUND OF THE INVENTION

1. Field of the Invention

The field of the invention is the providing of power for portable electronic devices, such as insulin pumps, analyte sensor devices, portable phones, personal digital assistants, etc. Specifically, the invention is directed to powering a portable electronic device for a known period of time after depletion of the main battery regardless of the type of battery that is installed in the portable electronic device.

2. Description of Related Art

Most portable electronic devices are powered by either an alkaline battery, a lithium-ion battery, or a rechargeable battery. FIG. 1(a) illustrates a voltage level over time provided by different types of batteries. As illustrated by Line A in FIG. 1(a), the alkaline battery starts out at a high voltage, e.g., approximately 1.55 volts, and decreases over time. Line D represents a battery threshold voltage. This low battery threshold voltage represents a value at which the battery is determined to be providing a low voltage. Once this threshold is reached, a message will need to be transmitted to a display of the portable electronic device indicating that the battery is running low, and should be replaced. If the portable electronic device is utilizing an alkaline battery, the voltage threshold may be around 1.16 or 1.08 volts. After the low battery threshold is reached in an alkaline battery, the alkaline battery can normally provide power to the portable electronic device for approximately twelve hours, assuming that the main battery life of the alkaline battery is 30 days. It should be noted that battery life is dependent on actual energy used by the device. Also, it also should be noted that due to the voltage threshold being around 1.1 volts, it is estimated that only two-thirds of the battery energy of the alkaline battery is utilized.

A lithium battery is capable of providing a much higher initial voltage and sustaining the value of that voltage for a long period of time. However, as illustrated by line B in FIG. 1(a), once the lithium battery becomes drained, the decrease in voltage value is rapid. If a lithium battery is being used in a portable electronic device, a user of the portable electronic device may have less than 30 minutes after receiving a low voltage message before the portable electronic device loses power. If the user is utilizing the portable electronic device for medical reasons, e.g., like an insulin pump, blood glucose sensor or meter, this may not provide the user with enough time to find a replacement battery.

A rechargeable battery can be a good economic solution for an owner of a portable electronic device. Rather than buying a new set of batteries every week or every month, the user may utilize household current to charge up the battery after the battery has expended its energy. Many portable electronic devices cannot utilize rechargeable batteries because the initial voltage supplied by the battery is too low and sometimes is not greater than the low battery threshold voltage set for alkaline batteries. The rechargeable battery has characteristics similar to the alkaline battery in terms of how long it can power a device, but as illustrated by Line C in FIG. 1(a), the initial voltage supplied by the rechargeable battery is lower than the initial voltage supplied by the alkaline battery. Accordingly, some initial voltages for rechargeable batteries may be lower than the low battery threshold voltage for the portable electronic device, as is mentioned above, and the portable electronic device may generate a message indicating that the rechargeable battery cannot be utilized. This is also true in regards to partially drained batteries, which may have low initial voltage readings.

In addition, the effective voltage of any of these batteries can be affected by the environment in which the battery is stored or utilized. For example, a temperature change in the environment in which the battery is located, can reduce the effective voltage provided by the battery. Also, subjecting the battery to vibration can result in a lowering of the effective voltage generated by the battery. This results in the battery providing a voltage reading that is lower than the low battery threshold and thus the portable electronic device may be unable to utilize the batteries subjected to changes in temperature as well as vibration.

Many current portable electronic devices that utilize a DC power source also include a backup battery system that provides a limited amount of functionality for the portable electronic device until the DC power source is replaced or recharged. In other words, the backup battery may provide enough energy to operate a run time clock for the portable electronic device and to save the contents of a memory, but does not provide power for full functionality of the portable electronic device.

BRIEF SUMMARY OF THE INVENTION

In accordance with embodiments of the invention, a method of providing backup power to a portable electronic device is provided. In embodiments of the invention a battery level of a primary battery is monitored. A disconnect signal is generated to cause the primary battery to be disconnected if the battery level of the primary battery is below a low battery threshold. A connection signal is generated to couple a backup battery to power the portable electronic device if the battery level of the primary battery is below the low battery threshold. The backup battery provides power for operating the portable electronic device for a predetermined minimum time regardless of what type of battery is utilized in the portable electronic device.

In further embodiments, the portable electronic device detects whether the main battery has been inserted into the portable electronic device and a detection signal is transmitted to a controller if the main battery is detected. If the main battery has been detected, a voltage output from the main battery is coupled to a power converter. The converter provides an operating voltage to the controller after receiving the voltage from the main battery. The controller charges a backup battery utilizing a signal transmitted from the controller. The controller monitors the battery level of the backup battery to determine if the backup battery has been fully charged. The controller disables charging of the backup battery if the charging level of the backup battery has been exceeded, which represents that the backup battery is adequately charged.

DETAILED DESCRIPTION OF THE INVENTION

In the following description, reference is made to the accompanying drawings which form a part hereof and which illustrate several embodiments of the present inventions. It is understood that other embodiments may be utilized and structural and operational changes may be made without departing from the scope of the present inventions.

Figure 1A:
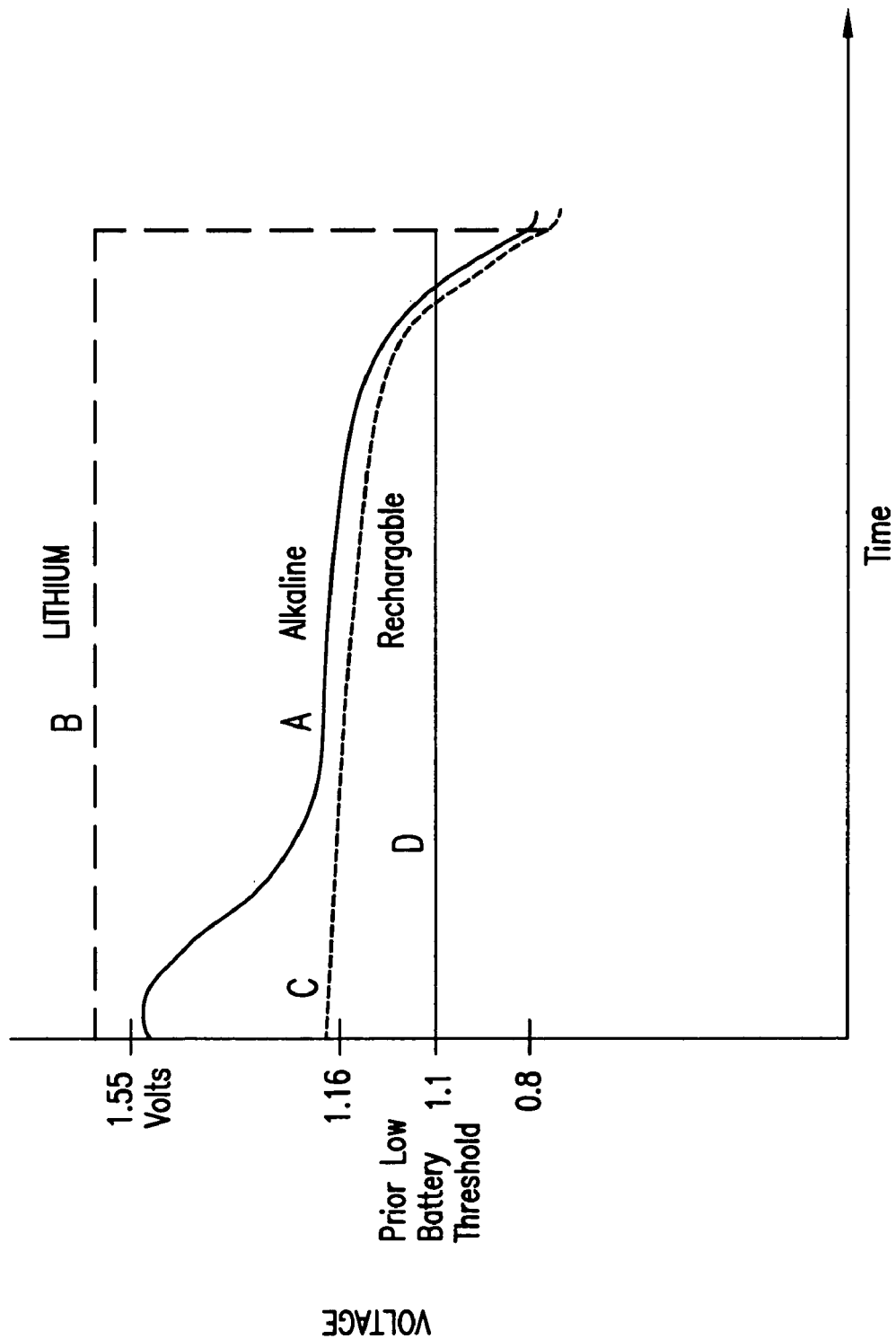
FIG. 1(a) illustrates a voltage level over time provided by different types of batteries.
Figure 1B:
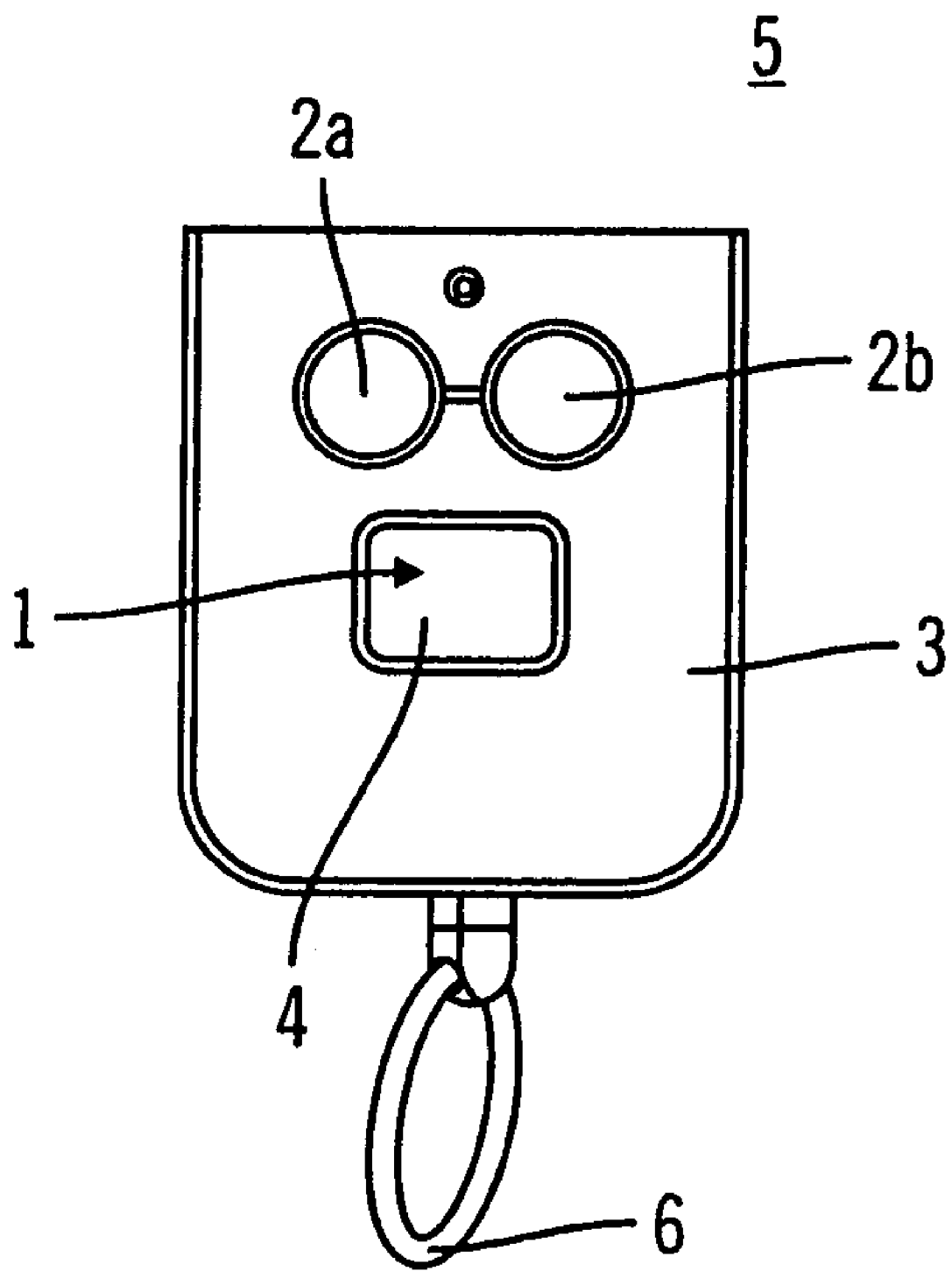
FIG. 1(b) illustrates a front view of a controller device according to an embodiment of the invention.

In one embodiment, the controller device is a hand-held device separate from the therapy/diagnostic device, such as an infusion device, that allows the user to communicate with the therapy/diagnostic device without actually handling the device. Other examples of therapy/diagnostic devices include electronic therapy devices and devices that receive diagnostic information from cardiac and other sensors. As illustrated in FIG. 1(b), the controller device 5 includes a housing 3 adapted to be carried by the user and a communication system (not shown) contained in the housing 3 for transmitting a communication or command from the user to the infusion device. In further embodiments, the controller device 5 may receive communications sent from the infusion device or other components of the infusion system, such as for example, a characteristic determining device. Further, the controller device may include one or more user input devices 2a and 2b on the controller device housing 3, such as keys, buttons, or the like, for the user to input data or commands. The controller device 5 includes a display 4 on the controller device housing 3 which simultaneously displays whatever information and/or graph is being displayed on the infusion device display at that moment. The display 4 allows a user to easily monitor and control what actions are taking place in, or being performed by, the infusion device. In some embodiments, the controller device 5 may further include a backlight 1 in the controller device display 4 for easier viewing. The backlight may be adapted to be in one or more colors, which can be user selectable for personalized use. In further embodiments, the backlight may be adapted to flash and/or turn to a color such as yellow or red when various alerts and alarms take place. In additional embodiments, the controller device 5 may include accessories such as hand straps 6 to provide convenient handling. In particular embodiments, the controller is sized smaller than 6 inches long by 4 inches wide by 1 inch thick.

In certain embodiments, a characteristic determining device that senses and determines the concentration of an analyte of a patient, for example blood glucose ("BG"), and controls the infusion device according to the measurements, may be included in an infusion system with the controller device and the infusion device. The characteristic determining device includes a housing, a receptacle coupled to the housing for receiving and testing an analyte from the user to determine a concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user. In particular embodiments, the characteristic determining device may also include a lancing device coupled to the receptacle for obtaining the analyte from the user.

In embodiments, the infusion device includes a housing adapted to be carried by the user, a drive mechanism contained in the housing and operatively coupled with a reservoir containing the fluid for infusing the fluid into the body of the user, a communication system-contained in the housing for receiving the communication including the data indicative of the determined concentration of an analyte in the user from a characteristic determining device, and a processor contained in the housing and coupled to the communication system for processing the data indicative of the determined concentration of the analyte in the user and controlling the infusion device. In particular embodiments, the infusion device is sized smaller than 6 inches long by 4 inches wide by 1 inch thick.

The infusion device may further include a bolus estimator used in conjunction with the processor for calculating an estimated amount of fluid to be infused into the body of the user based upon the received data indicative of the determined concentration of the analyte in the user and a target concentration of the analyte in the user, and an indicator to indicate when the estimated amount of fluid to be infused has been calculated. The system may determine the concentration of one of any variety of analyte types including, but not limited to, oxygen, blood, temperature, lactase, pH, implantable, and the like. Additionally, the infusion device may include a user input device, such as keys, buttons, or the like, for inputting an estimate of a material to be ingested by the user, and the bolus estimator may include the capability to calculate the estimated amount of fluid to be infused into the body of the user based upon the inputted estimate of the material to be ingested by the user. The infusion device may also include a memory for storing the data indicative of the determined concentration of the analyte in the user received by the infusion device communication system from the determining device communication system.

In still further alternative embodiments, the characteristic determining device is a BG measurement device and may use samples from body fluids other than blood, such as interstitial fluid, spinal fluid, saliva, urine, tears, sweat, or the like. In yet other alternative embodiments, other measurement devices may be utilized to determine the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like. In still other alternative embodiments, other fluids may be delivered to the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. Particular embodiments are directed towards the use in humans; however, in alternative embodiments, the infusion devices may be used in animals. For pain management, a bolus function may be set up as a Patient Controlled Analgesic (PCA) function for customized delivery or the user may press a preset bolus button several times.

In other embodiments, the characteristic determining device is a BG meter that determines BG level and the infusion device is an insulin infusion pump. The BG meter communicates the measurement of BG to the infusion pump device to determine the amount of insulin for delivery to the user. In alternative embodiments, the BG measurement device may be a continuous glucose measurement system, a hospital hemacue, an automated intermittent blood glucose measurement system, and the like, and/or the BG measurement device may use other methods for measuring the user's BG level, such as a sensor in contact with a body fluid, an optical sensor, a RF sensor, an enzymatic sensor, a fluorescent sensor, a blood sample placed in a receptacle, or the like. The BG measurement device may generally be of the type and/or include features disclosed in U.S. patent applications Ser. No. 09/377,472 filed Aug. 19, 1999 and entitled "Telemetered Characteristic Monitor System and Method of Using the Same," Ser. No. 09/334,996 filed Jun. 17, 1999 and entitled "Characteristic Monitor with a Characteristic Meter and Method of Using the Same," Ser. No. 09/487,423 filed Jan. 20, 2000 and entitled "Handheld Personal Data Assistant (PDA) with a Medical Device and Method of Using the Same," and Ser. No. 09/935,827 filed Aug. 23, 2001 and entitled "Handheld Personal Data Assistant (PDA) with a Medical Device and Method of Using the Same," which are herein incorporated by reference. Such BG measurement devices may be adapted to be carried by the user, for example, in the hand, on the body, in a clothing pocket, attached to clothing (e.g., using a clip, strap, adhesive, or fastener), and the like. In particular embodiments, the BG measurement device is sized smaller than 6 inches long by 4 inches wide by 1 inch thick.

Figure 2:
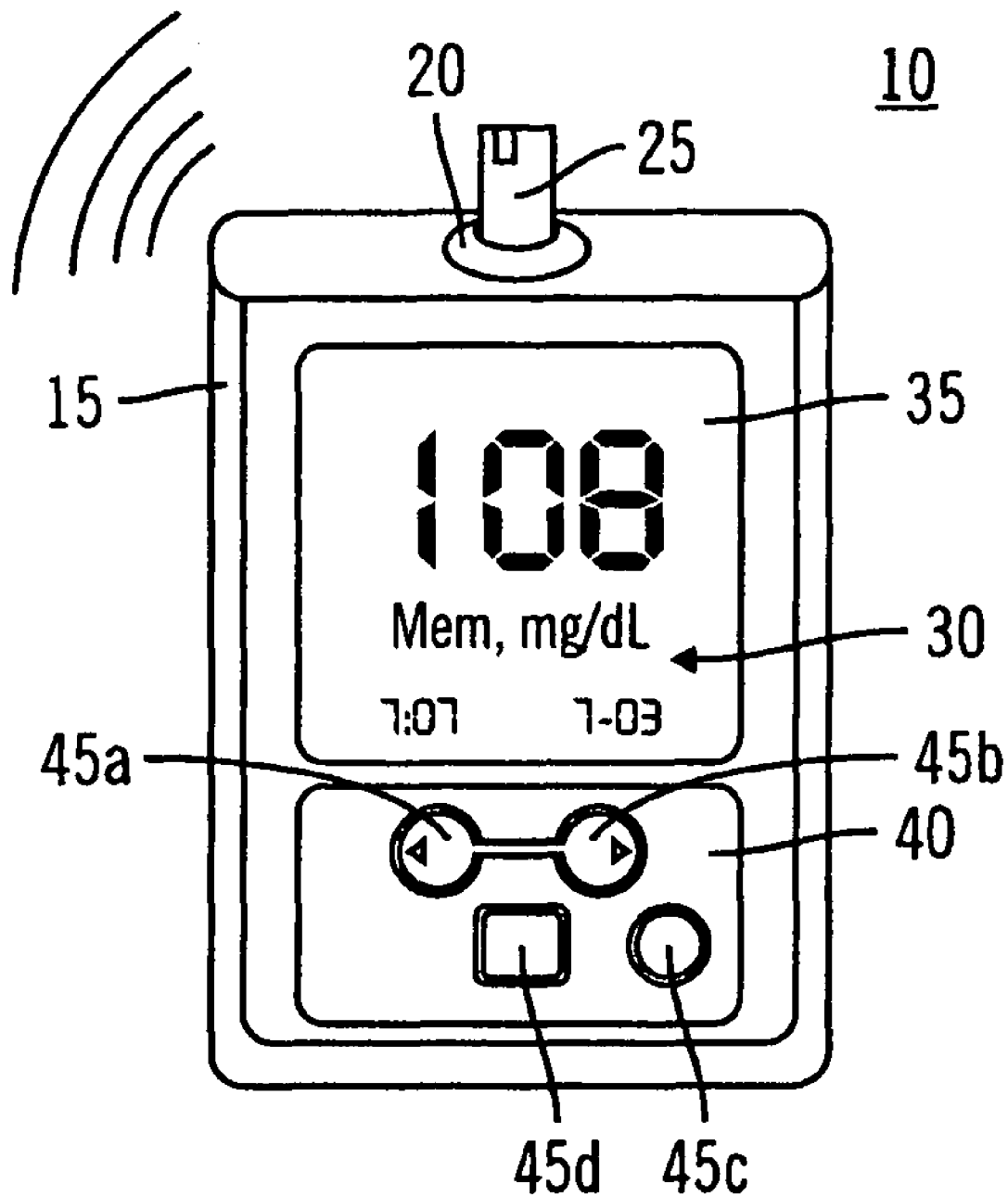
FIG. 2 illustrates a front view of a blood glucose meter integrated into the controller device housing according to an embodiment of the present invention.

In alternative embodiments of the invention, the BG meter may be integrated into the controller device housing, as shown in FIG. 2, where the controller device housing 15 includes a BG meter receptacle 20. The controller 10 includes a housing 15 adapted to be carried by the user, a BG meter receptacle 20 coupled to the housing 15 for receiving and testing BG level from the user to determine a concentration of the BG in the user. A BG test strip 25 that holds a use blood sample is inserted into the BG meter receptacle 20 for the testing by the controller device 10. In variations, the controller device 10 may have a cartridge-like mechanism which loads and presents the strip for testing and then ejects it. The controller device 10 has a display 30 on the housing 15 to show information requested by the user or an instructed act that was undertaken by the infusion device, such as for example, determined concentration of blood glucose levels, BG trends or graphs, such as described and disclosed in U.S. patent application Ser. No. 10/624,177, entitled "System for Monitoring Physiological Characteristics," which is herein incorporated by reference. The display 30 may further include a dedicated backlight 35 to facilitate viewing. The backlight 35 may be a user programmable multi-color backlight that additionally performs the function of a visual indicator by flashing colors appropriate to the level of an alert or alarm. The backlight 35 may also have variable intensity (automatic or manual) to preserve the battery power and improved viewing. The controller 10 includes a keypad 40 on which various input devices, such as keys, buttons, or the like, are located. The keypad buttons 45a, 45b, 45c, and 45d are used by the user to select options and/or input information.

The power of the controller device and of the other various devices discussed herein may be provided from a battery. The battery may be a single use or a rechargeable battery. Where the battery is rechargeable, there may be a connector or other interface on a device to attach the device to an electrical outlet, docking station, portable recharger, or so forth to recharge the battery while in the device. It is also possible that a rechargeable battery may be removable from the device for recharging outside of the device, however, in some cases, the rechargeable battery may be sealed into the housing of the device to create a more water resistant or waterproof housing. The devices may be adapted to accommodate various battery types and shapes. In further embodiments, the devices may be adapted to accommodate more than one type of battery. For example, a device may be adapted to accommodate a rechargeable battery and, in the event of battery failure or other need, also adapted to accommodate a readily available battery, such as a AA battery, AAA battery, or coin cell battery.

Figure 3:
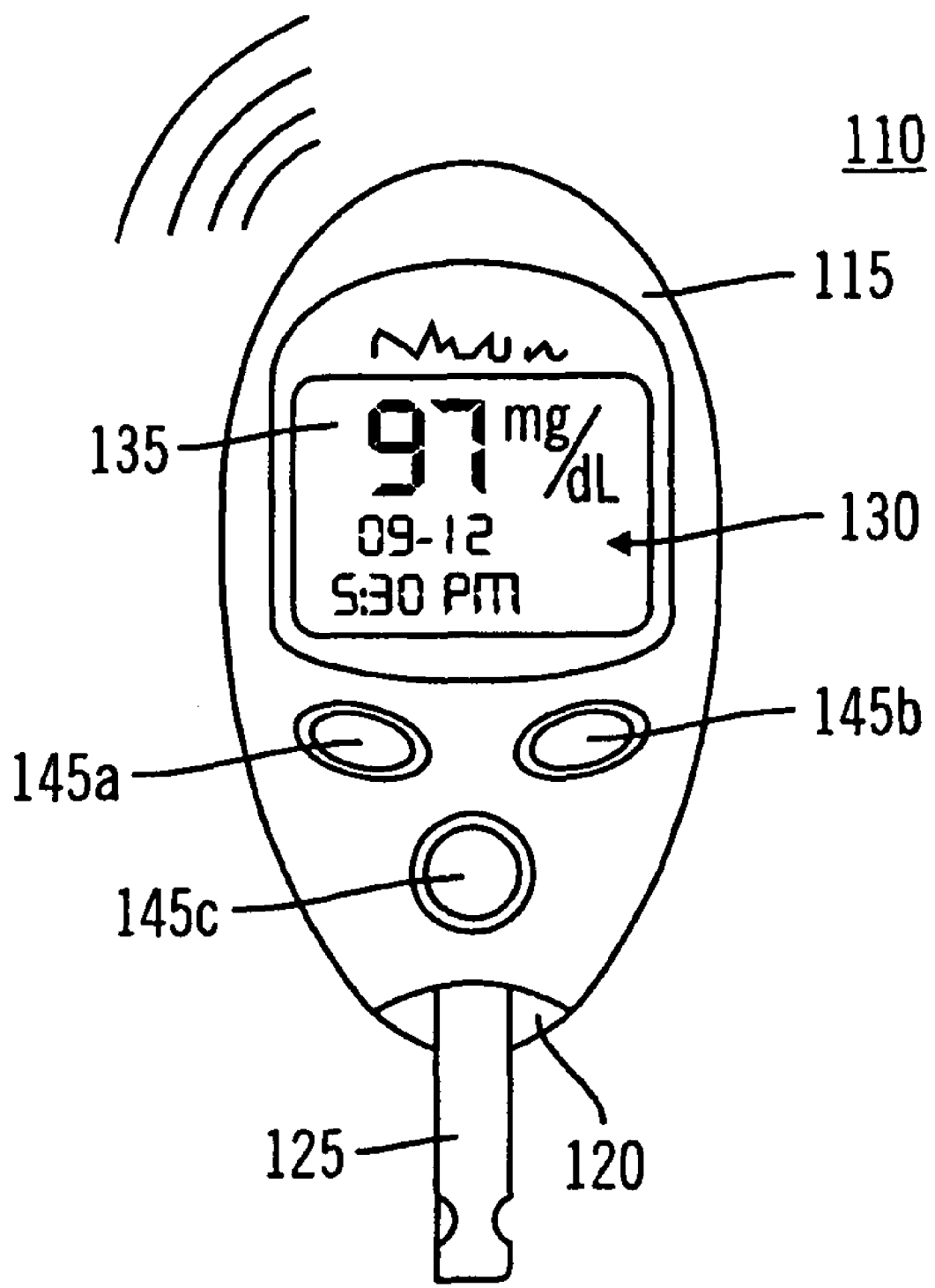
FIG. 3 is a front view of a blood glucose meter integrated into a controller device housing according to an embodiment of the present invention.

In FIG. 3, another embodiment of a controller device is shown. Again, the controller device 110 includes a housing 115 adapted to be carried by the user, and a BG meter receptacle 120 coupled to the housing 115 for receiving and testing BG level from the user to determine a concentration of the BG in the user. A BG test strip 125 that holds a user's blood sample is inserted into the BG meter receptacle 120 for the testing by the controller device 110. The controller device 110 has a display 130 on the housing 115 to show information requested by the user or an instructed act that was undertaken by the infusion device, such as for example, determined concentration of blood glucose levels, graphs of blood glucose level trends or fluid delivery information. The display 130 may include a dedicated backlight 135 to facilitate viewing. The controller device 110 includes a few input devices, such as keys, buttons, or the like, on the housing 115. The housing buttons 145a, 145b, and 145d are used by the user to select options and/or input information.

Figure 4:
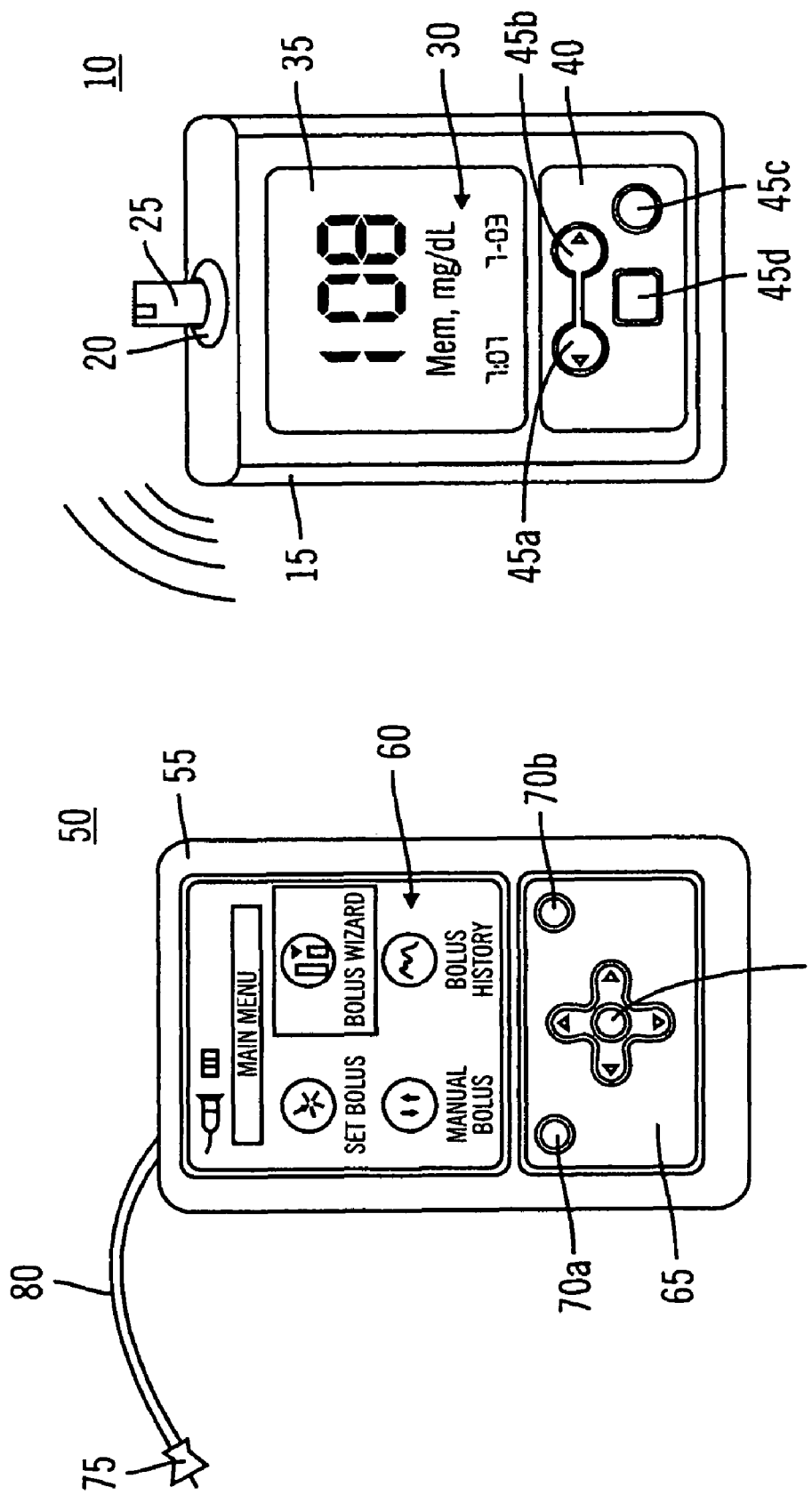
FIG. 4 is a front view of a blood glucose meter integrated into a controller device housing communicating with an infusion device according to an embodiment of the present invention.

FIG. 4 illustrates an embodiment of an infusion system that includes an infusion device 50, and further includes a controller device integrated with a BG meter 10, where both share one housing. The controller device 10 communicates to the infusion pump device 50 through a wireless method, for example RF signals. The controller device 10 senses and determines the concentration of BG level of a patient and controls the infusion device 50 according to the measurements. This substantially reduces, if not eliminates, calculations on the part of the patient. In particular embodiments, the infusion device 50 includes a housing 55 adapted to be carried by the user. On the housing 55 there is included a display 60 that, like the BG meter display 30, shows information requested by the user or an instructed act that was undertaken by the infusion device 50. The infusion device 50 may not include a display, but in that case there should be a suspend/resume input and an action input for safety reasons. The BG meter display 30 shows information according to communications sent to the controller device 10 from the infusion device 50. At any moment, the display 60 of the infusion device 50 may show substantially the same information as shown on the controller device display 30. The two displays may mimic one another so that the user may choose to conveniently view the selected information from the controller device 10 rather than the infusion device 50, which is usually attached to the user's body through the infusion set 75. The infusion device 50 delivers fluid from within the housing 55, through tubing 80 and into the infusion set 75 into the user's body at an infusion site. Further included on the infusion device 50 is a keypad 65 with various input devices, such as the keypad buttons 70a, 70b, and 70d illustrated in the figure.

Figure 5:
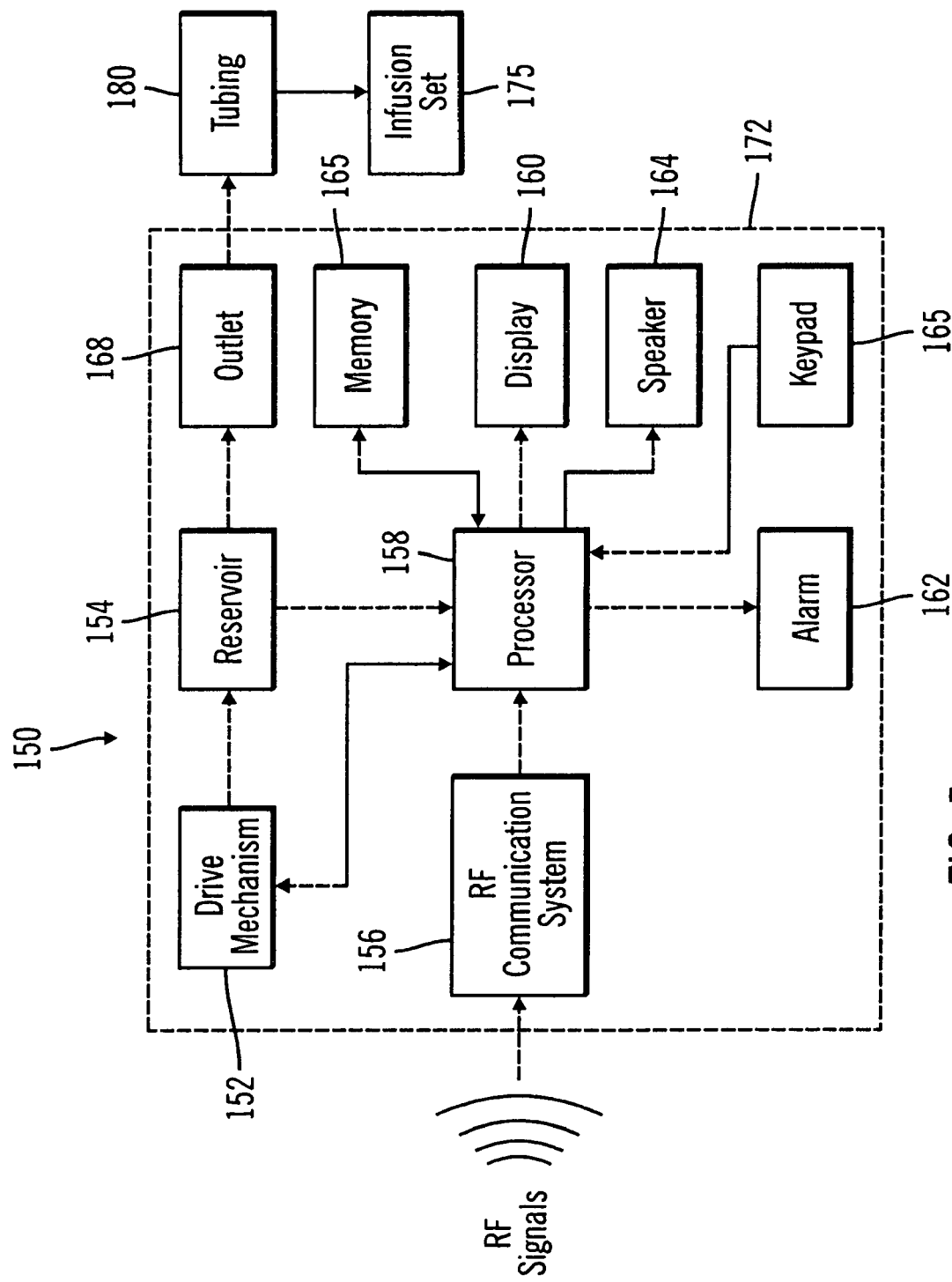
FIG. 5 provides a block diagram of a RF communication system in the infusion device according to an embodiment of the present invention.

FIG. 5 provides a block diagram of the infusion device 150. The infusion device 150 includes a drive mechanism 152 contained in the housing 172 and operatively coupled with a reservoir 154 containing the fluid for infusing the fluid into the body of the user, a communication system 156 contained in the housing 172 for receiving the communication from the controller device including data indicative of the determined concentration of the BG in the user from the BG meter, and a processor 158 contained in the housing 172 and coupled to the communication system 156 for processing the received communications and controlling the infusion device 150. The fluid is delivered from the reservoir 154 through an outlet 168 in the housing 172 and into the user's body via the tubing 180 and infusion set 175. The infusion device 150 may further include an indicator displayed on the display 160 to indicate when the estimated amount of fluid to be infused has been calculated. Additionally, the infusion device 150 may include one or more user input device(s), such as keys, buttons, and the like, for inputting an estimate of a material to be ingested by the user, and the estimated amount of fluid to be infused into the body of the user may be based upon this inputted estimate of material to be ingested. A bolus estimator may be used in conjunction with the infusion device processor for estimating the appropriate amount of fluid to be infused into the body of the user. There may be included a keypad 165 on which the one or more input device(s) are located. The infusion device 150 may also include a memory 166 for storing the data received by the infusion device communication system 156 from the controller device communication system.

In further embodiments, a speaker 164 is included to provide an alternative mode of communication. In an embodiment, the infusion device 150 may display a message that states "move nearer to pump" when the BG meter or controller device senses that the communication with the infusion device 150 is weak or interrupted. A similar message may be displayed if the BG meter or controller device senses some type of problem or malfunction. Alternatively, an alarm 162 may alert the user of any problem or malfunction by vibrating, emitting warning sounds, flashing light, and the like. In further embodiments, the infusion device 150 may provide other functions that show a variety of other displays, for example, when the last bolus was administered, when the last alarm occurred, when the last finger stick was taken, past trends, all alarms that occurred in a time period, calibrations, meals, exercise, bolus schedules, temporary basal delivery, and the like. Whenever a bolus is being delivered, the infusion device 150 can send a message every time a tenth of a unit, or some specified amount, is delivered.

Figure 6A:
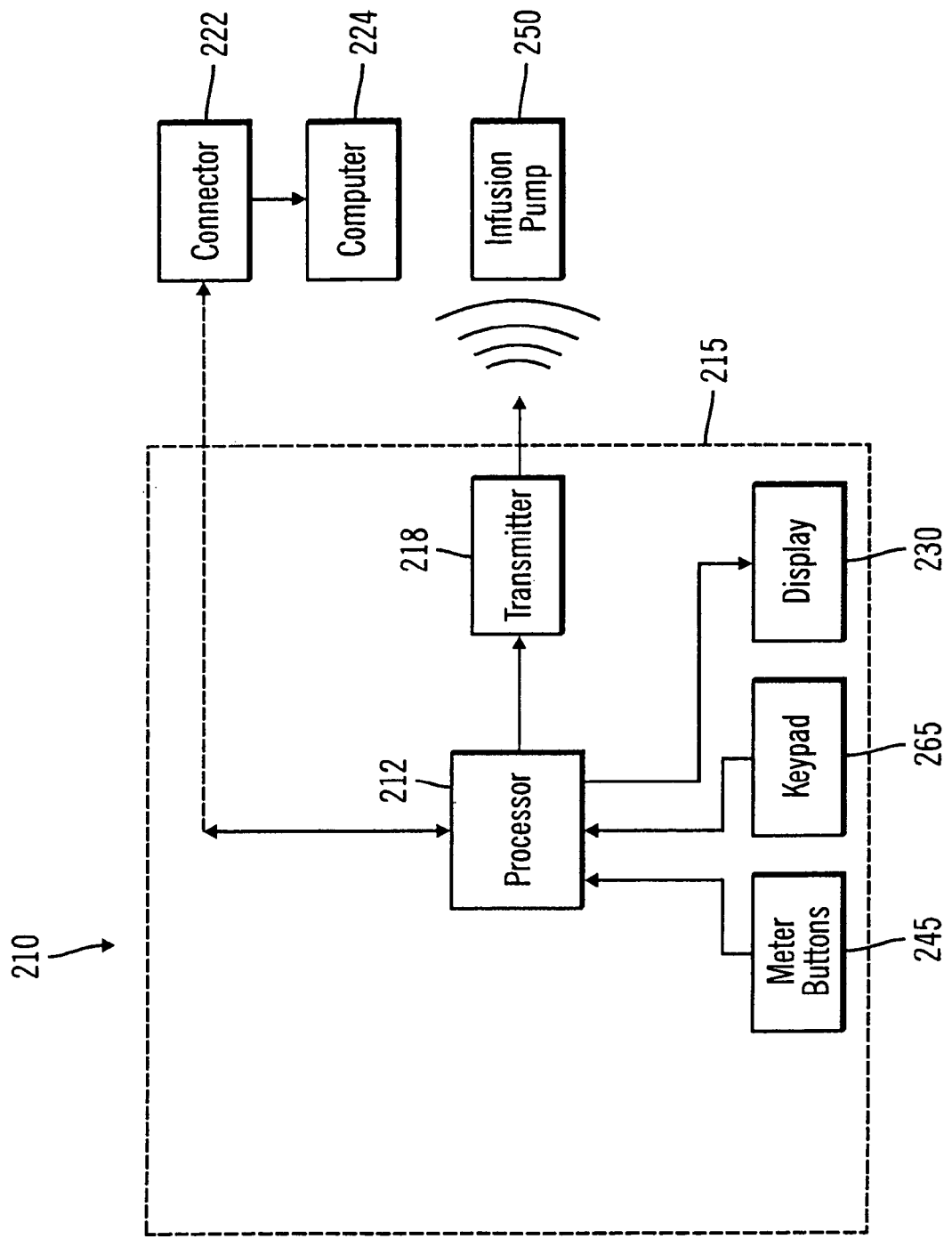
FIG. 6a is a block diagram of a the controller device according to an embodiment of the present invention.
Figure 6B:
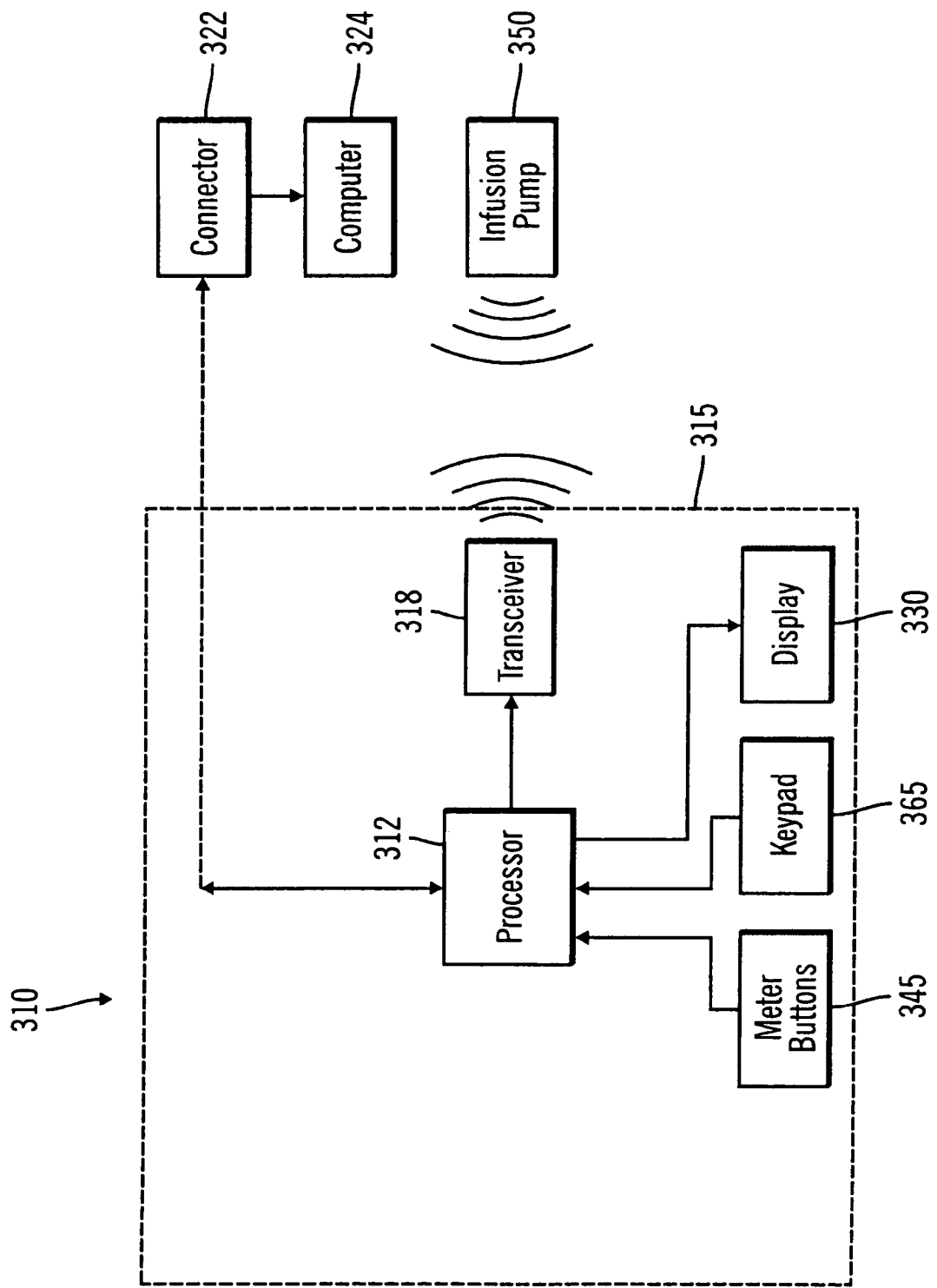
FIG. 6b is a block diagram of a controller device according to an embodiment of the invention.

As seen in FIG. 6a, the controller device 210, includes a housing 215 adapted to be carried by the user. A processor 212 contained in the housing 215 is adapted to process data and commands inputted by the user, and a transmitter 218 (or a transceiver 318 (as shown in FIG. 6b)) contained in the housing 215 and coupled to the processor 212 transmits such communications, including data indicative of the determined concentration of the BG in the user, to the infusion device 250. In further embodiments, the controller device 210 may be integrated with a BG meter in one housing, which has a lancing device and receptacle for BG test strips, for obtaining a BG sample from the user.

The controller device 210 may communicate with a remote station, such as a computer 224, through a data transfer system, using a type of communication connector 222, that couples the controller device 210 to the computer 224 and allows the data downloading. Alternatively, communication may be by wireless methods, such as RF, IR, Bluetooth or other wireless methods. Data may be downloaded via the RF telemetry in the same manner as data is transferred from the controller device 210 to the infusion pump device 250. The transmitter 218 (or a transceiver 318 (as shown in FIG. 6b)) converts RF signals into compatible electrical pulses that may be subsequently sent through a serial port to a specified destination. Data, including software upgrades and diagnostic tools, may also be downloaded via RF telemetry, or any other wireless or wired method, from a remote station, such as the computer 224, to the infusion device 250. Other remote stations include, but are not limited to, a hospital database, a cellular telephone, a PDA, a smart phone or internet. For example, a cellular phone may be used as a conduit for remote monitoring and programming. In one embodiment, the controller device may be configured so as to have cellular telephone capabilities. In further embodiments, the controller device and/or the other devices with display may be capable of providing PDA functions as well, removing the need for patients to carry separate PDA devices.

The controller device 210 includes on the housing a display 230 that may mimic the display on the infusion pump device 250. The controller device display 230 shows information according to communications sent to the controller device 210 from the infusion device 250. At any moment, the display of the infusion device 250 may show substantially the same information as shown on the controller device display 230. In some embodiments, whatever is shown on the infusion device 250 corresponds to that shown and reflected on the display 230 of the controller device 210. In this manner, the user may more conveniently view what is being processed or acted upon in the infusion pump device 250 without removing or adjusting the infusion pump device 250 to view the display. In embodiments, the controller device 210 may include one or more input device(s) 245, such as keys, buttons, and the like, on a keypad 265 so that all, or substantially all, viewing and data entry may be performed on the same device without moving the infusion pump device 250.

Figure 7:
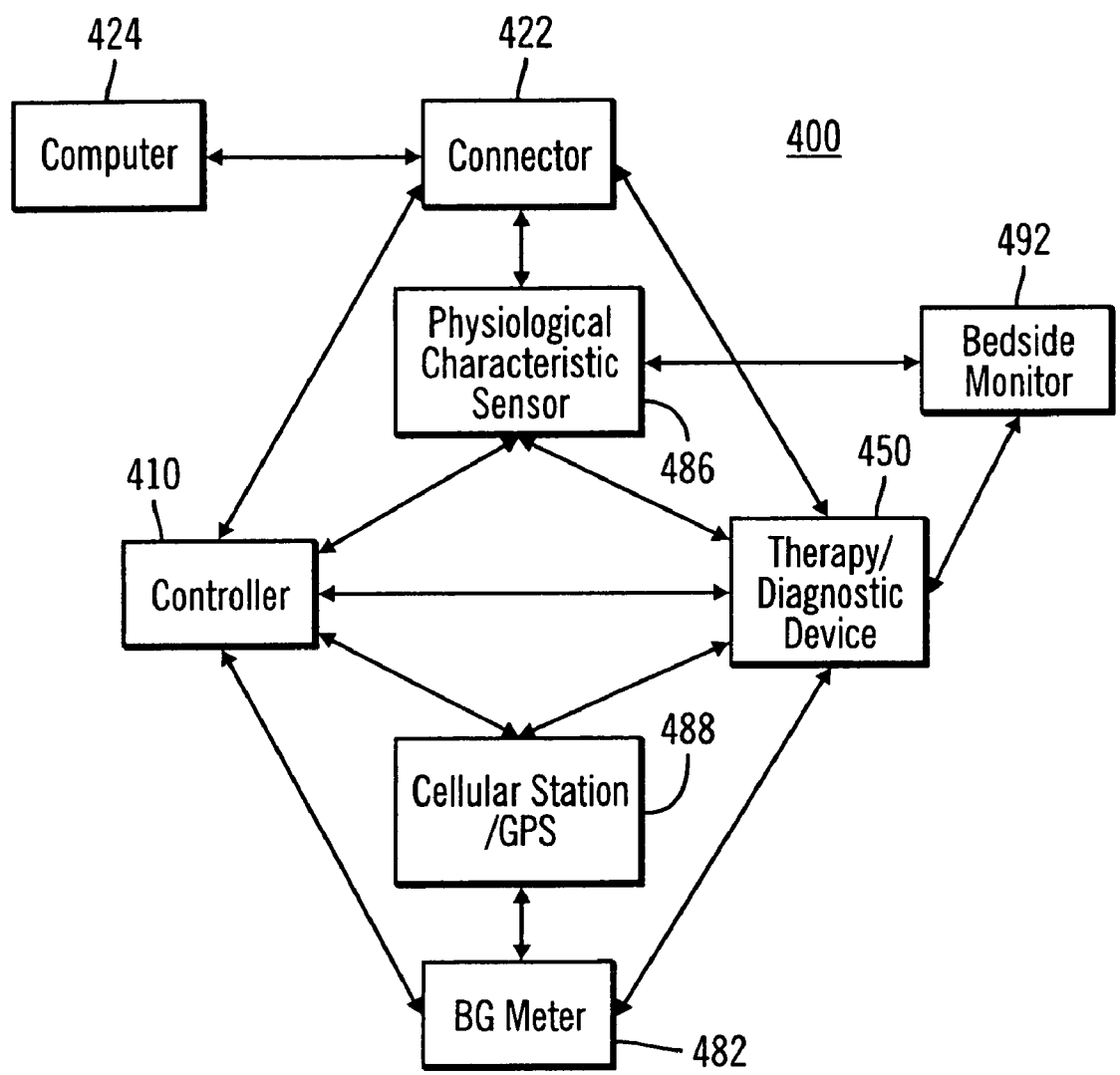
FIG. 7 is a block diagram of communication paths within the infusion system according to an embodiment of the present invention.

The infusion pump device 250 and the controller device 210 need to have substantially the same resolution or else the screen may not be presented correctly on the display. Another difficulty may be in properly displaying the scaling of graphs. This issue may be addressed by having the infusion pump device talk in an "ideal" screen, and not necessarily in its actual screen format. As shown in FIG. 7, the potential communication paths within embodiments of the infusion system are illustrated. The controller device 410 may serve as a translator between the infusion device 450 and the other components of the infusion system 400, such as a BG meter 482. For example, the controller device 410 may have the ability to determine how best to translate the infusion device's 450 description to the screen of the two displays. As can be seen, the infusion device 450 may communicate directly with the BG meter 482. In alternative embodiments, the resolution need not be the same, and the infusion device and/or controller can compensate for the resolution difference so that one or the other may utilize enhanced displays or a simple display depending on the devices and the needs of the user.

In some embodiments, the infusion system 400 may include multiple controllers that can communicate with one infusion device 450. In other embodiments, there is one controller 410 communicating to one infusion device 450. The controller may also be integrated into the infusion device in some embodiments. In yet another embodiment, the BG meter 482 may be integrated into the controller 410, sharing one housing, to both communicate with the infusion pump device 450. In this embodiment, the controller is separate from the infusion pump device. In this embodiment, the infusion device 450 serves as the central hub with most of the intelligence of the system 400. In yet another embodiment, the controller device 410 may be a key fob, in which case, the controller device 410 would serve simply as a virtual keyboard to input data and commands to the infusion device 450. Optional peripheral devices may include a physiological characteristic sensor device, such as a telemetered glucose monitoring system (TGMS) sensor. Alternatively, the sensor may be directly wired to a monitor/user interface. The TGMS sensor or physiological characteristic sensor 486 may provide for continuous BG monitoring. The physiological characteristic sensor 486 may also be linked to a bedside monitor 492 so that monitoring and programming of medication delivery may be performed remotely. In some embodiments, the infusion pump device does not include, nor need, a display. In this embodiment, a key fob may serve as a remote display. Other options for a remote display include, but are not limited to, cellular telephones, computer monitors, PDA's, smart phones, watch remotes, and the like. The infusion device 450 may further communicate with, and download data such as software upgrades and diagnostic tools from, a remote station like a computer 424 from a connector 422. Optionally, the infusion device 450 may also communicate with the controller device 410 through a station such as a cellular station 488 that includes GPS. In further embodiments, the connector 422 may have memory capability to transport data.

In the above embodiment, the control is maintained in the central hub and the infusion pump device 450 sends out most of the commands. The infusion device 450 also sends requests to receive specific data from the controller device 410. The controller device 410 and the infusion pump device 450 may communicate to one another by a connector 422, other wired methods or by wireless methods, such as RF, IR, Bluetooth, or other wireless methods. In other embodiments, the infusion pump device 450 may contain all or substantially all of the intelligence. The controller device 410 may be limited in the amount of time that they communicate with one another to save power in the controller device 410. For example, RF communications may be minimized, such that the marriage between the infusion pump device 450 and controller device 410 occurs once. The information regarding the screens displayed is sent to the controller device 410, and when the infusion pump device 450 needs to display a screen, it sends a screen number to the controller device 410. In the case of screen displays, if the data being sent is fixed, then the screen can be simply displayed. If the data is variable, then the variable data is sent with the screen to the infusion pump device 450. The screen is then displayed based on a combination of the fixed screen information and the variable data. Exchange IDs, strings to be displayed, and foreign languages are among data that may be sent from the controller device 410. Further commands that may be sent from the infusion pump device 450 include, among other commands, a command to show a specific screen on the controller device 410, a command for displaying requested information on the screen, a command for showing the rules for the input devices, a command for showing the intelligence about that screen type (e.g., menus, data entries, etc.), and the like. The devices may all send diagnostic information to each other, and particularly to the controller device, so that the user may see if anything is going wrong with any of the devices.

Figure 8:
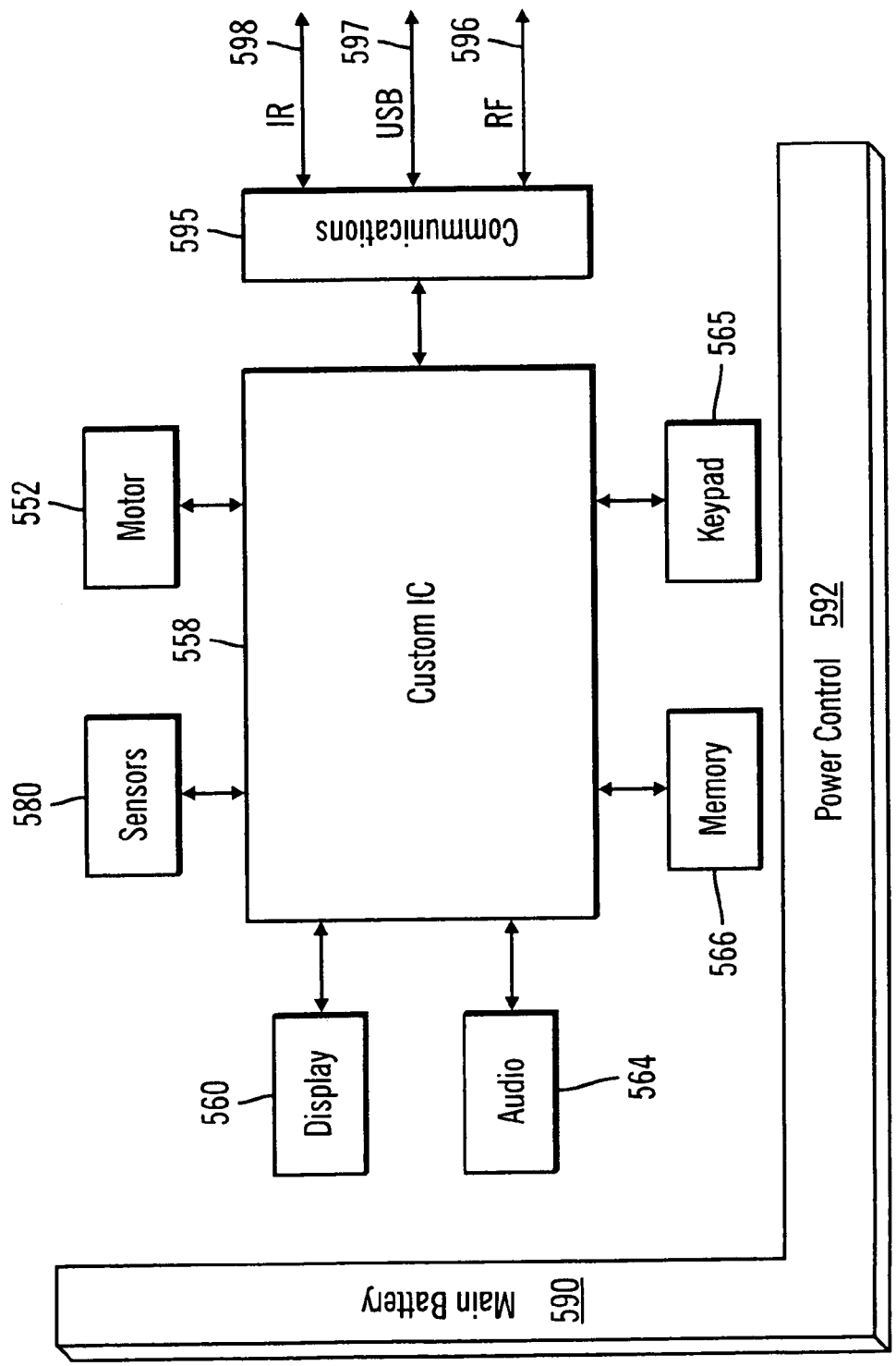
FIG. 8 is a diagram of an electronics architecture according to an embodiment of the invention with a custom integrated circuit.

FIG. 8 shows an electronics architecture according to an embodiment of the invention with a custom integrated circuit ("custom IC") 558 as the processor. This architecture can support many of the devices discussed herein, for example the controller device, the infusion device, the characteristic determining device, a BG meter, or any combination of the above. The custom IC 558 is in communication with a memory 566, keypad 565, audio devices 564 (such as speakers or audio electronic circuitry such as voice recognition, synthesis or other audio reproduction), and a display 560. Where there is a drive mechanism in a device that includes infusion functions, the custom IC 558 is in communication with a motor 552 or motor drive circuitry or other means of delivering fluids or therapy via an electromechanical means. Where there are one more sensors included in the device, or in communication with the device (such as a characteristic determining device or a device which includes a characteristic determining function), the custom IC 558 is in communication with the sensors 580. The electronics architecture further may include a communications block 595 in communication with the custom IC 558. The communications block 595 may be adapted to provide communication via one or more communications methods, such as RF 596, a USB 597, and IR 598. In further embodiments, the custom IC 558 may be replaced by electronic circuitry, discrete or other circuitry, with similar functions.

The electronics architecture may include a main battery 590 and a power control 592. The power control 592 may be adapted to give an end of battery warning to the user, which pan be predicted based on the type of battery used or can be calculated from the power degradation of the battery being used. However, in certain embodiments it is not necessary to know the type of battery used to create an end of battery warning. Various battery types, such as rechargeable, lithium, alkaline, etc., can be accommodated by this design. In certain embodiments, the electronics architecture includes a removable battery and an internal backup battery. Whenever a new removable battery is inserted, the internal backup battery will be charged to full capacity and then disconnected. After the removable battery has been drained of most of its energy, it will be switched out of the circuit and the internal backup battery will be used to supply power to the device. A low battery warning may then be issued. The internal backup battery may be rechargeable. In further embodiments, a supercap, for example, is used to handle the peak loads that the rechargeable internal battery could not handle directly, because it has sufficient energy storage. This method also allows the use of any type of removable battery (alkaline, lithium, rechargeable, etc.) and partially drained batteries. Depending on use, the backup battery may allow the device to operate for at least one day after the removable battery has been drained or removed. In further embodiments, a microprocessor measures the charge states and control switches for removable and internal backup batteries. These embodiments of the invention are discussed in detail below.

In certain embodiments, the controller device has no user settings and very little memory, because all, or substantially all, needed data and instructions will be sent to the controller device by the infusion pump device. Thus, the functions are all, or substantially all, contained on the infusion pump device in such embodiments.

In alternative embodiments, the infusion pump device may include expanded capabilities, such as color on the display screens, and more graph options that can present more detailed graphs. For example, there may be included a graph called "mobile day" where the BG levels of the user for the past five days may be shown as overlapping graphs. The mobile day graph allows the user to see the trend in BG level changes during those days, and aids the user in better controlling the insulin delivery according to the trends that appear for specific times of each day.

The BG meter may also include expanded capabilities, such as for example, voice synthesis, voice activation, polyphonic speakers for the vision impaired, and plugs on the BG meter for headphones. Likewise, the controller device may also be configured to provide these expanded capabilities.

As described above, the controller device may be integrated with the BG meter in some embodiments. In those embodiments, the input keys and the display will all, or substantially all, be included on the controller device. The BG meter may also be separate from the controller device and may talk directly to a sensing device, such as a TGMS sensor. The TGMS sensor is inserted into the subcutaneous tissue of the user to read body fluids, and allows for continuous blood glucose monitoring. The readings are used in conjunction with the BG level determined by the BG meter to continuously monitor BG levels through extrapolating the BG measurements. This embodiment would be compatible with users that do not have an infusion pump device, in which case, there is a need for the ability to talk directly to the TGMS sensor without talking to the infusion pump device.

If the BG meter talks to the TGMS sensor then the TGMS sensor may broadcast the data received from the BG meter to the infusion pump device and the controller device. In some embodiments, the infusion pump device will always send the data to the controller device. In the case that the controller device does not receive the information from the infusion pump device, it will assume that the infusion pump device has not received the data and will communicate the value to infusion pump device. In other embodiments, the infusion pump device, controller device and TGMS sensor maintain a three-way communication with one another, and have the ability to check the contacts between one another. In still further embodiments, the system is set up to automatically call for assistance when analytes reach a certain level. The call may include a GPS location.

In an embodiment of the present invention, the graph displayed on the controller device may display information regarding boluses, finger sticks, exercise, meals and the like. In one embodiment, the graph displayed has eight segments, representing different limits and an actual BG line. In other embodiments, the graphs may include additional time spans for which to show the varying BG levels. For example, the embodiments may include a 3 hour, 6, 12, and 24 hour graphs. Additional features of the graphs may include the ability to zoom in or out of the graph. There may be included an ESC key that will allow the user to return to the last scale. Other options may allow the user to focus on specific positions on a graph. In yet another feature, the user can select the resolution in which to view the graph.

In a situation where the infusion pump device and the controller device are out of sync, e.g., the graph on the pump and the graph on the controller device do not look substantially the same, there needs to be a way to resynchronize the two components if something goes wrong. For example, if finger stick values do not both have current finger stick values, then the graphs for the controller device and the infusion pump device would be different.

There also may be some type of positive mechanism for the controller device if the communication between the controller device and the pump are interrupted. For example, the mechanism may have the controller device stop displaying its graph in a "time-out" phase for the time the infusion pump device screen is absent or no more data is entered by the user for a period of time. In this case, the infusion pump device operates on the last data that the infusion pump device sent to the controller device to display. In an embodiment, the controller device will display an idle screen during the time-out phase and while the communication between the infusion pump device and the controller device is re-established. The idle screen may remain until the next action is selected by the user. After the time-out phase, the user may press a key to start up the communication again. Once a key is pressed, the controller device will process the key data and the screen will be displayed. The controller device may periodically send signals to the pump to see if it is still active on the screen.

In alternative embodiments, there will be a positive confirmation requested prior to displaying graphs. For example, the graphs may be shown in bitmap packets (e.g., bit-by-bit), and if the user will be getting a large number of packets of data, for example 15 packets of data, to show the graph, the user may opt not to confirm. The data is passed from the controller device, which is programmed to display the data, to the infusion pump device. The controller device can operate in graphics description language where data is recognized by the controller device as instructing it on which position to put each line or color and the graphics display would handle determining the resolution that the graph would be displayed in. In some embodiments, the graph may be displayed in three-dimensional format.

The specific screens to be displayed may include fixed menus, partially variable menus, and variable menus. In fixed menus, the menus do not change depending on data. Therefore, they will always look substantially the same on the screen, and the controller device may be programmed to display them when requested. The fixed menus may be described as screen numbers. In this way, the controller device can easily request "screen 1" or "screen 2." In fixed menus, the text is defined once. There may also be menus where menu items appear and disappear depending on the current settings of the infusion pump device. These menus are considered partially variable menus because some data appear and disappear, and are not all fixed. For example, a program for bolus setup allows a user to change current bolus settings. Bolus set up menus involve variable information as well as fixed information. The values may be variable, but the main menu items (title of variables, etc.) will stay the same. Variable menus contain information that is completely variable, e.g., bolus history screen. Variable data is sent at the time of the screen display, and there is generally no fixed text. What is displayed in variable menus depend on what bolus action the user selects. The history screens resemble the menu screens in that the user cannot select and input any information with the history screen. Data entry screens, on the other hand, include multiple fields on a screen and can accept data selection and input by the user.

Different units may need to be switched dynamically in depending on how the type of entry is communicated. The screens may also need to be able to display minimum and maximum values as well as time increments, to ensure precision of the display. The rules for this translation will be defined in the infusion pump device. Likewise, for a dual-wave bolus, there must be defined how the values interlock. Sensor high and low BG values also need to be interlocked (in some embodiments, these two values will be displayed in the same screen).

In one embodiment, communication between the infusion system components takes place when the user presses one or more keys to send data to the infusion pump device and, in response, the infusion pump device can relay to the controller device to instruct on what to display. Alternatively, the user may input data through scrolling down menus and selecting options. When the user prompts, the controller device, for example by pressing an "ACT" button, the controller device will then tell the infusion pump what to do, e.g., deliver fluid to the user.

In its most simplest form, the controller device is a display only, used to show a BG value and/or graph. In another simple form, the controller device embodies only a virtual keypad that may mimic exactly the buttons on the infusion device. When the user presses a key on the controller device, the controller device tells the infusion device what button was pressed and the infusion device acts as if the button was pressed on the infusion device itself. Each component of the infusion system may be of different degrees of sophistication. For example, the controller device can range from a simple key fob with limited capabilities and with, for example, one or two keys to a complex device with memory, many keys and advanced graphing options. In a complex form, the controller device may embody all or substantially all of the intelligence that is present in the infusion device. In this form, the controller device could do all calculations, graphing functions, and other data input, output, and manipulation at the controller device. The controller device would then send data to the infusion device indicating what the controller device had done so that the infusion device could be put into the same state as the controller. It is possible for the controller device to have many different degrees of computing intelligence, so that few, none, many, or all computing may be done at the controller device. How much intelligence will be in the controller device may depend on battery life, size requirements, and so forth.

In further embodiments, the processor of the controller device has unique identification information, and the communication transmitted from the controller device to the infusion device further includes the unique identification information of the controller device processor such that the infusion device is capable of discerning whether the communication is intended for receipt by the infusion device. In yet further embodiments, the processor of the infusion device has unique identification information, and the communication transmitted from the controller device to the infusion device further includes the unique identification information of the infusion device processor such that the infusion device is capable of discerning whether the communication is intended for receipt by the infusion device.

Additionally, both the controller device and the BG meter may communicate over wireless networks. Some examples include RF, IR, Bluetooth, spread spectrum communication, and frequency hopping communication. In further embodiments, there may be a "Listen Before Talk" scheme where the system selects the cleanest of allotted channels through which to communicate. Further examples include giving the controller device cellular telephone or pager capabilities. In the alternative, the communication may be wired, such as in hospital use. In a wired embodiment, there may be a tether physically connecting the infusion pump device to the controller device and/or BG meter. In yet another alternative, the controller device and the infusion pump device could be both wired and wireless—when wired, the two components communicate by wire, and when disconnected, the two components could operate through wireless communication.

In another wireless example, if the user has access to a computer network or phone connection, the user can open communication via the internet to obtain communications from, and send communications to, a nurse, parent, or anyone so desired. As discussed above, a transceiver may be used to facilitate data transfer between the PC and the infusion pump device. Such a communication may also be used by a party, other than the user, to control, suspend, and/or clear alarms. This embodiment could be very useful for a parent to monitor the infusion system of a child, or for a physician to monitor the infusion system of a patient. The transceiver may allow patients at home or clinicians in a hospital setting to communicate with the various components of the infusion system via RF telemetry. The transceiver may be used to download device information from the pump and sent to the PC when the transceiver is connected in to the serial port of the PC. In embodiments, the transceiver may derive its power from the PC when the two are connected. In this way, the transceiver conveniently does not require a separate power source. In another embodiment, a cellular phone may be used as a conduit for remote monitoring and programming. In yet other embodiments, the controller device with a BG meter may also act as a transceiver, which would eliminate an extra component.

In further embodiments, the controller device communication system is capable of being deactivated and reactivated. The controller device may include input devices, such as keys, buttons, and the like, for inputting commands, and the communication system of the controller device is capable of being deactivated in response to a first command from the user input device and being reactivated in response to a second command from the user input device. Alternatively, the communication system of the controller device may be automatically reactivated after a predetermined amount of time has elapsed or at a predetermined time of day.

In an embodiment of the present invention, the processor of the infusion device uses power cycling such that power is periodically supplied to the communication system of the infusion device until a communication is received from the controller device. When a communication is received from the controller device, the processor of the infusion device discontinues using power cycling so that the power is continuously supplied to the infusion device communication system. The infusion device processor may then resume using power cycling upon completing the receipt of the communication including the data indicative of the determined concentration of the analyte in the user from a BG meter communication system.

In yet another embodiment, the infusion system may include a bedside monitor. The monitor could communicate through the same avenues as the BG meter, the controller device, and the infusion pump device. The monitor could be used, as described above, to remotely alarm people other than the user, such as for example, parents, physicians, nurses, and the like. This would provide an extra layer of monitoring for the user, especially when the user is alone. In further embodiments, the system may be set up so that multiple devices are placed around the house. This would provide easy access to monitor the diabetic. Additionally, the parent will be able to obtain data to monitor a child user at home and when the parent is away. Such home monitors could be set to any mode preferred, for example, flashing lights, warning sounds like beeping, vibration, and the like. Other features may include a function that allows the remote user (parent, physician, nurse, etc.) to change and/or deliver a bolus from remote sites.

In an alternative, the controller device may be configured so as to have cellular telephone capabilities. The cellular network could provide a conduit for remote monitoring and programming. Additionally, the cellular network could be used to notify parents, physicians, or emergency services of alarms or alert states. A button may be included on the controller device and/or the infusion device to automatically alert a parent, physician, or emergency services when pressed. For example, a monitoring device may be built directly into a patient's cellular telephone so that in the case of a hypoglycemic event, an alarm or connection may be made to emergency services via the cellular telephone. In a further embodiment, GPS technology may also be built into the cellular telephone to allow easy location of the patient. Alternatively, GPS technology may be included in the controller device without cellular telephone technology. In other embodiments, the GPS technology may also be built into the infusion pump, BG meter or controller device.

The infusion system may be part of a closed-loop system, such as an implantable infusion system with a sensor system or an external infusion device with a sensor system. In such a system, there may be included safety nets, such as alarms and automatic shut-offs.

The alarms may be customized to specific user needs. The alarm may be set to flashing lights for the hearing impaired, or warning sounds and/or vibration for the vision impaired. There could further be included headphones that can plug into the controller device for vision impaired to instruct the user on what to do in the case that an alarm goes off. The headphones could also be plugged into a MPEG player or the like. To avoid having the pump broadcast information, the alarms may be handled in a way where the user presses a button on the controller device. Alarms could also be included on the pump. There may further be included a turn-off option where, if there is a need to communicate with the controller, the user can choose a selection to turn off the controller. In further embodiments, there may be included a feature in any of the devices including an alarm where when the device has sounded an alarm for a period of time and the user has not responded, the alarm will switch to a vibrate mode and/or will attempt to signal companion devices in the system to alarm the user.

It is noted that some users can be expected to have somewhat diminished visual and tactile abilities due to the complications from diabetes or other conditions. Thus, the display and buttons or other input devices may be configured and adapted to the needs of a user with diminished visual and tactile abilities. In alternative embodiments, the high level module (and/or the low level module) may communicate to the user by audio signals, such as beeps, speech or the like.

Other display settings may be customizable, including, but not limited to, the background, sounds, fonts, and wallpaper. There may be a children's mode, with limited features available so that a child cannot dispense too much medication at once. Different display features may be included in the module and/or may be downloaded from a computer. The high level module may have a memory with which to store customized settings or pump control. The memory may be of any type that is known in the art, such as a volatile or non-volatile memory. Both a volatile and non-volatile memory may be used, which can speed up operation of the pump. As an example, non-volatile memories that could be used in the invention include flash memories, thumb drives and/or memory sticks such as USB thumb drives, removable hard drives, and optical drives.

In some embodiments, the language that the controller device operates in may comprise several different languages, ranging from 1 language to about 40 languages and potentially more. To set language, data must be first initialized to modify the phrases and detail font that may be significantly different in one language as compared to another language. For example, some languages, such as Chinese, are read in vertical columns, from the right to the left, and thus, needs to be displayed in such manner. One way to overcome this complication in using different languages is to have fonts built into the infusion pump device. Because fonts are now described in pen strokes (true-type fonts), rather than in pixels (bit-by-bit) this allows the infusion pump device to determine out how to display the different fonts. Another option could involve uploading the fonts in strings from various sources, such as the internet.

If so desired, a food library may be downloaded from a PC, or from the internet via a PC. In the food library, each food item will have some information associated with it, for example, carbohydrate count, fat count, proteins, serving size, and the like. The food library may be built directly into the infusion pump device, or it may be downloaded from remote sources, as discussed above. For one example, the food library may be downloaded through a transceiver embodied by the user's cellular telephone. Other options may include eliminating the need to bypass the transceiver every time a food item is selected, such as, downloading the food items from the PC and storing it until use. The food library may also be input directly into the controller device rather than the infusion pump device. If the food library is contained in the infusion pump device, an associated food library menu could be dynamic. The user could select from different layers of the food library the items consumer or about to be consumed and the infusion pump device could calculate the appropriate amount of insulin to be delivered. Variable data could be included for a small food library with less than 50 food items. For example, there could be variable data for a food library dedicated to breakfast foods only. There could be a "breakfast" key or icon on the controller device that the user can select. There may also be "lunch" and "dinner" and "snack" icons.

Communications between the system components may be performed in a variety of manners. In an embodiment using RF options, there could be employed a single frequency or a "spread spectrum" where a large range of RFs can be used to relay the communication. In another embodiment, changing frequencies can be used so as to pick up whatever frequency is present. This is known as "frequency hopping," where the frequency changes every millisecond or so to take advantage of all, or substantially all, frequencies available. In some cases, frequency hopping allows the system to find frequencies that are not being used by other nearby systems and thus avoid interference. In addition, a system may operate in a manner where each component-to-component communication is on a different frequency, or where the delay for each communication is different. Other types of RF, that are not described, may also be used for communication, such as, translation frequency.

According to yet another embodiment of the present invention, an infusion system includes a controller device, with a controller device display, and an infusion device, with an infusion device display, and a method for infusing a fluid into a body of a user is provided. The method includes the steps of: receiving data communication from a user, transmitting with the controller device the communication including data to an infusion device, receiving with the infusion device the communication, and displaying with the controller device display information regarding the fluid delivery, where the display on the controller device display shows information according to instructions or communications sent to the controller device from the infusion device. At any moment, the display of the infusion device may correspond with what is displayed on the infusion device display. The method may further include the step of displaying a trends and graphs. Additionally, the method may include the step of inputting an estimate of a material to be ingested by the user, and the estimated amount of fluid to be infused into the body of the user is calculated further based upon the inputted estimate of the material to be ingested by the user.

Although the above description has been focused on use of a controller device with an infusion device, it is appreciated that a controller device as described herein could be used with any number of therapy/diagnostic devices. For example, in any case where a therapy/diagnostic device is tethered to the body, at least partially implanted in the body, or otherwise inconvenient for the user to manipulate while therapy or diagnosis is being performed, a controller device may be used that can send commands to the therapy/diagnosis device and/or mimic the display on the therapy/diagnosis device. Therapies other than infusion of fluids could include electrical therapy, such as electrical therapy for the brain and for conditions such as epilepsy. Diagnostics could include any number of diagnostics, such as information from cardiac and other sensors.

Electrical therapy devices include neurostimulation devices for epilepsy, similar devices for pain management, etc. In addition, there are electro-acupuncture devices, where a needle is inserted into the body much like acupuncture, but additional therapy is delivered by electrical impulses. In certain embodiments, the structure of an electrical therapy device may include a needle that is inserted into appropriate areas of the body. The architecture would be similar to that of the devices described above. The patient/user would use the controller device to deliver "dosages" of electrical impulses to alleviate pain and manage neurological symptoms on demand such as twitching, uncontrolled movement of limbs, spasms, and so forth.

In further embodiments, devices such as those used in physical therapy clinics could be adapted for individual use. For example, a patch or other device placed on the body could be activated by the controller device to delivery said therapy, be it ultrasound, heat or some other media. The architecture for these devices could be similar to the architecture of the devices already described, where a physiological characteristic sensor or infusion device is replaced by a therapy delivering device/mechanism.

A portable electronic device may receive power from a removable main battery and/or a backup battery. In this embodiment of the invention, if a new removable main battery is inserted into a portable electronic device, an internal backup battery may be charged to full capacity. After the internal backup battery is charged to full capacity, the internal backup battery is disconnected. After the removable main battery has been drained of most of its energy, the main battery may be switched out of the circuit and the internal backup battery is used to supply power to the device. At this time, an indication of a low battery voltage is issued. A super capacitor (super cap), charged by the backup battery, may have enough energy storage to handle the peak loads that a rechargeable internal battery cannot handle directly. This method allows the use of any type of removable battery (alkaline, lithium, or rechargeable) and partially drained batteries. Depending on the use, the backup battery should allow the device to operate for a known amount of time after the removable main battery has been drained or removed. A controller would measure the charge states and operate the control switches for the removable main battery and internal backup battery.

Although a controller is identified above as performing action for measuring charge states and operating control switches, a microcontroller, logic, control circuitry, or application specific integrated circuits (ASICs) may be utilized to perform the same actions or other actions below described as being performed by the processor. Further, a processor, which loads operating software from a location outside of the processor may also perform the actions described above and below that are controlled by the controller. From this point forward, the term controller is utilized but a microcontroller, logic, control circuitry, ASIC(s), or a processor may be utilized to control the same actions.

The portable electronic device may be a portable personal medical device, such as an insulin pump, a glucose sensor, a transmitter, a pacemaker, or any type of medical monitor. In addition, the portable electronic device may be a cellular phone, a personal digital assistant, a digital music player, or a Blackberry or Treo type device. The present invention applies to any portable electronic device that is powered or can be powered by a removable battery and a backup battery.

Figure 9:
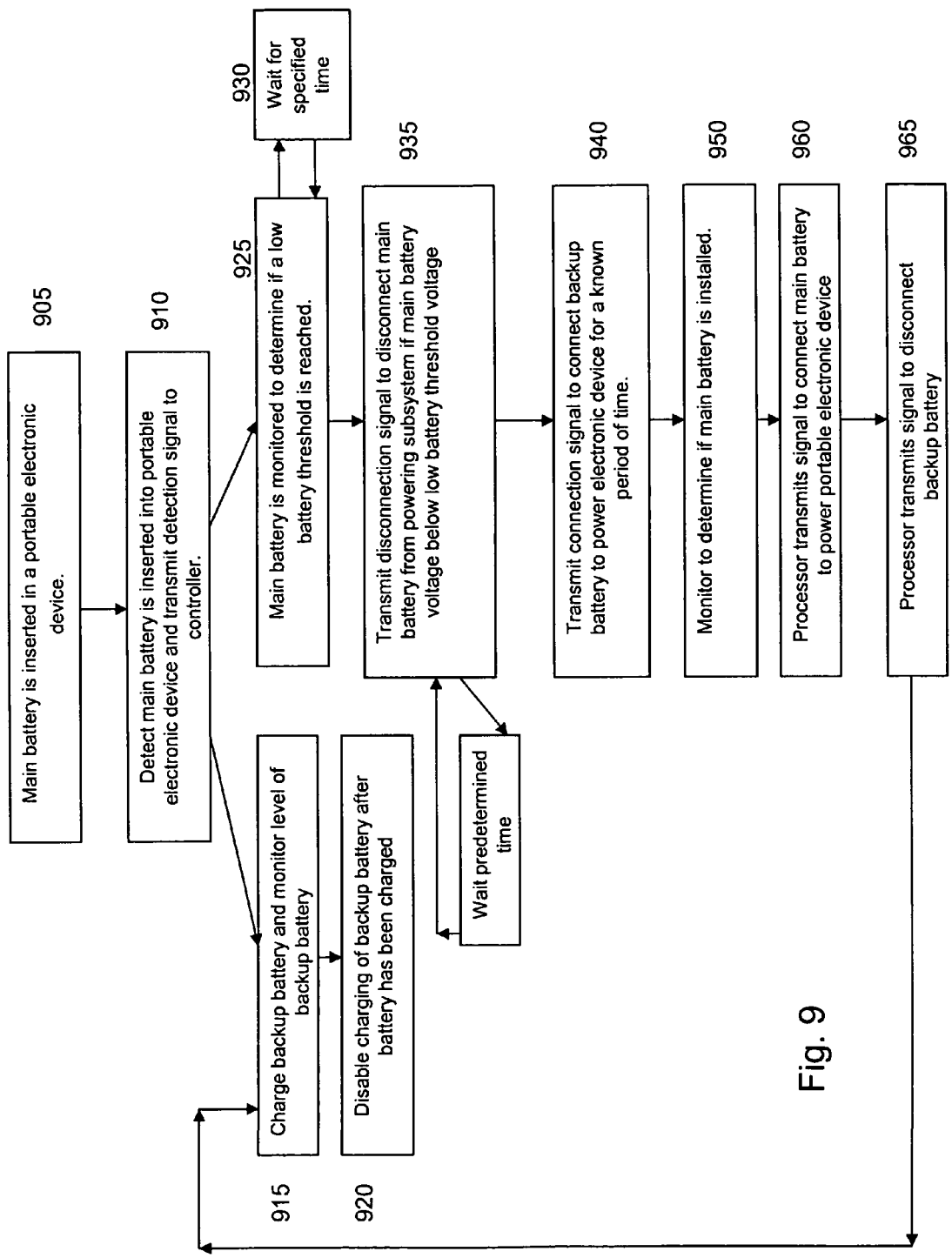
FIG. 9 illustrates a method to provide full functioning power to a portable electronic device after a main battery has reached a low voltage threshold according to an embodiment of the present invention.

FIG. 9 illustrates a method to provide full functioning power to a portable electronic device after a main battery has reached a low voltage threshold according to an embodiment of the present invention. In an embodiment of the invention, a main battery is inserted 905 into a power circuit for the portable electronic device. The main battery may be an alkaline battery, a lithium ion battery, or a rechargeable battery. NiCad, NMH, and Lithium batteries are examples of rechargeable batteries.

A main battery detection circuit in the portable electronic device may detect 910 that the main battery has been inserted into a power circuit and may transmit 910 a power detection signal to a controller or processor of the portable electronic device indicating that a main battery has been detected in the portable electronic device. In an embodiment of the invention, a polarity detection circuit may detect if the battery has been inserted incorrectly. In this embodiment of the invention, the portable electronic device may issue an error message instructing that the battery be placed in the portable electronic device correctly. In an embodiment of the invention, the portable electronic device may compensate for the incorrectly inserted battery. This may occur by a circuit or module in the portable electronic device reversing the coupling of the battery power into a power circuit of the portable electronic device.

In an embodiment of the invention, the controller may receive the battery detection signal. After receiving the battery detection signal, the controller may transmit a charge signal or a charging voltage 915 to the backup battery. In other words, the backup battery is being charged through an output of the controller. Accordingly, the backup battery is being charged indirectly by the main battery because the main battery is supplying power to the controller, which in turn supplies power to the backup battery.

In an embodiment of the invention, the controller may monitor charging 915 of the backup battery. Once, the backup battery is determined to be charged, the controller may disable charging 920 of the backup battery. In an embodiment of the invention, the controller may determine that a backup battery is charged based on a time measurement or calculation. In other words, the controller may wait a specific period of time (e.g., 24 hours, 48 hours, 12 hours) and then cease to send a charging signal to the battery. In an embodiment of the invention, the controller may monitor a voltage or current of a backup battery. Once the backup battery reaches a charging threshold voltage or current, the controller may cease to supply power to the backup battery. In an embodiment of the invention, the controller may monitor a voltage of the backup battery and after a specific period of time, e.g., 24 hours, 30 hours, or 40 hours, even if the backup battery voltage is not measured to be above the threshold, the controller may stop providing power to the backup battery. In an embodiment of the invention, the charging of the backup battery may take one day or two days. The time required for charging of the backup battery depends on how long the backup battery is utilized for powering the portable electronic device. The charging of the backup battery may, for example, utilize between 2-5% of the main battery's voltage. Under certain operating conditions, the charging of the battery may occur at the time when the main battery is providing power for the portable electronic device.

The main battery is monitored 925 to determine if the main battery voltage has decreased or has been drained and if a low voltage battery threshold has been met. In an embodiment of the invention, the controller monitors a voltage of the main battery and determines whether or not the main battery voltage has reached a low main battery threshold. In one embodiment of the invention, the low main battery threshold may be 0.8 volts. The low battery threshold voltage can be 0.8 volts because it allows a larger percentage of the battery energy to be utilized as compared to prior art systems where the low battery threshold voltage is approximately 1.1 volts. In other words, in previous portable electronic device systems, a message would be transmitted indicating low battery at 1.1 volts (and in some cases disabling the device). This message would be sent out although as much as $\frac{1}{3}^{rd}$ of the battery energy still remained. Illustratively, the low battery threshold voltage may be any value less than 1.0 volt. This is significant because the portable electronic device can run to a lower main battery voltage because a backup battery is present within the system and will provide power to maintain full functionality of the portable electronic device after the main battery has been drained. In an embodiment of the invention, the backup battery may provide the power or voltage for a known minimum time. This results in more energy of the main battery being utilized before the battery has to be replaced or recharged. For example, in prior art systems, about two-thirds of the battery's energy was typically utilized, while with the invention, greater than 95% of the battery's energy may be utilized. In an embodiment of the invention, the low battery threshold can be set to a specific level or to the same level for all of the different types of batteries, e.g., alkaline, rechargeable, or lithium. Illustratively, the low battery threshold voltage for the main battery may be 0.8 volts or any other voltage less than 1.0 volt.

If the main battery is still outputting a voltage, above or greater than the low voltage threshold, a predetermined amount of time is counted 930, and then the main battery is monitored again to determine if the main battery voltage has decreased below the low voltage threshold. In an embodiment of the invention, if the controller determines that the main battery is operating above the low voltage threshold, the controller may wait a specified amount of time, e.g., 1 second, 5 seconds, 15 seconds, 1 minute, or 5 minutes, and may again monitor the voltage of the main battery after the specified amount of time has elapsed.

If the main battery is not operating above the low voltage threshold, the controller transmits 935 a disconnect signal to disconnect the main battery from the powering circuit of the portable electronic device. In an embodiment of the invention, the controller may transmit a signal to a switch to close, which results in the main battery being coupled to ground. At this time, the main battery is not providing power for the portable electronic device. Under these operating conditions, the removable main battery can be recharged or replaced.

At approximately the same time or alternatively, in the same timeframe, if the main battery voltage has decreased below the low voltage threshold, the controller transmits 940 a connection signal to connect the backup battery to the powering circuit of the portable electronic device. In other words, the controller transmits a signal to connect the backup battery. In an embodiment of the invention, the controller or processor may transmit a signal to close a switch to couple the battery into a circuit for powering the portable electronic device. In an embodiment of the invention, the backup battery may be placed into circuit such that the backup battery is in parallel with a capacitor (which may be referred to as a super capacitor or supercap). In an embodiment of the invention, the capacitor or super capacitor may be charged up by the backup battery and may provide power to a boost converter. In an embodiment of the invention, the main battery is also in parallel with the supercap, and the supercap may be charged by the main battery. In an embodiment of the invention, after the backup battery is switched into powering the portable electronic device, the controller may transmit a message indicating an amount of time for which the backup battery is capable of powering the portable electronic device. This may be a minimum time that the backup battery can provide time for the portable electronic device based on a maximum potential current draw of the portable electronic device.

The backup battery itself is not utilized to power the electronic circuits and components because the backup battery does not provide smooth enough power for the electronic circuits and components of the portable electronic device. In other words, there may be spikes or ripples within the voltage provided by the backup battery. This may also be true with the main battery because the main battery may not provide smooth or stable power for the electronic circuits and components of the portable electronic device. The boost converter provides power for a large number of electronic components (e.g., processors, motors, display modules) in the portable electronic device. The backup battery supplies power to the supercap to allow for full functionality of the portable electronic device. In other words, all of the operating features of the portable electronic device can be utilized even when the portable electronic device is being powered by a backup battery. The powering of full functionality of the portable electronic device in the present invention is unlike many prior art systems where the backup battery provides power only for a run-time clock and for storing system settings in a CMOS memory. In an embodiment of the invention, the backup battery is able to provide full-functioning power to the portable electronic device for a predetermined time, (e.g., 24 hours when normal battery life for a battery is 30 days). The battery life is dependent on the average energy usage by the portable electronic device. In another embodiment of the invention, the backup battery provides power to allow for full functionality of the portable electronic device for 48 hours (e.g., this is dependent upon the average energy use of the device). Longer timeframes, such as 24 or 48 hours, allow a user of the portable electronics device to continue to operate the portable electronic device with a sense that the device will not lose power and still have time to find a replacement main battery and/or to recharge the main battery. This is important for persons who utilize portable electronic devices in remote areas where a new battery or recharging for a rechargeable battery is not available. It is also important for people who utilize portable electronic devices in medical applications where constant power to the portable electronic device is essential along with knowing approximately how long the portable electronic device can operate utilizing the backup battery.

After the backup battery has been connected to power the portable electronic device, the controller continues to monitor 950 the main battery to determine if a new or recharged main battery is connected to the charging circuit of the portable electronic device. Once the controller determines a sufficiently charged or new main battery has been installed, the controller transmits 960 a signal to connect the main battery to the charging circuit. The controller also transmits 965 a signal to disconnect the backup battery from providing power to the portable electronic device. The controller also begins to charge 915 the backup battery, as is described above. The controller also starts the monitoring of the main battery voltage.

Figure 10:
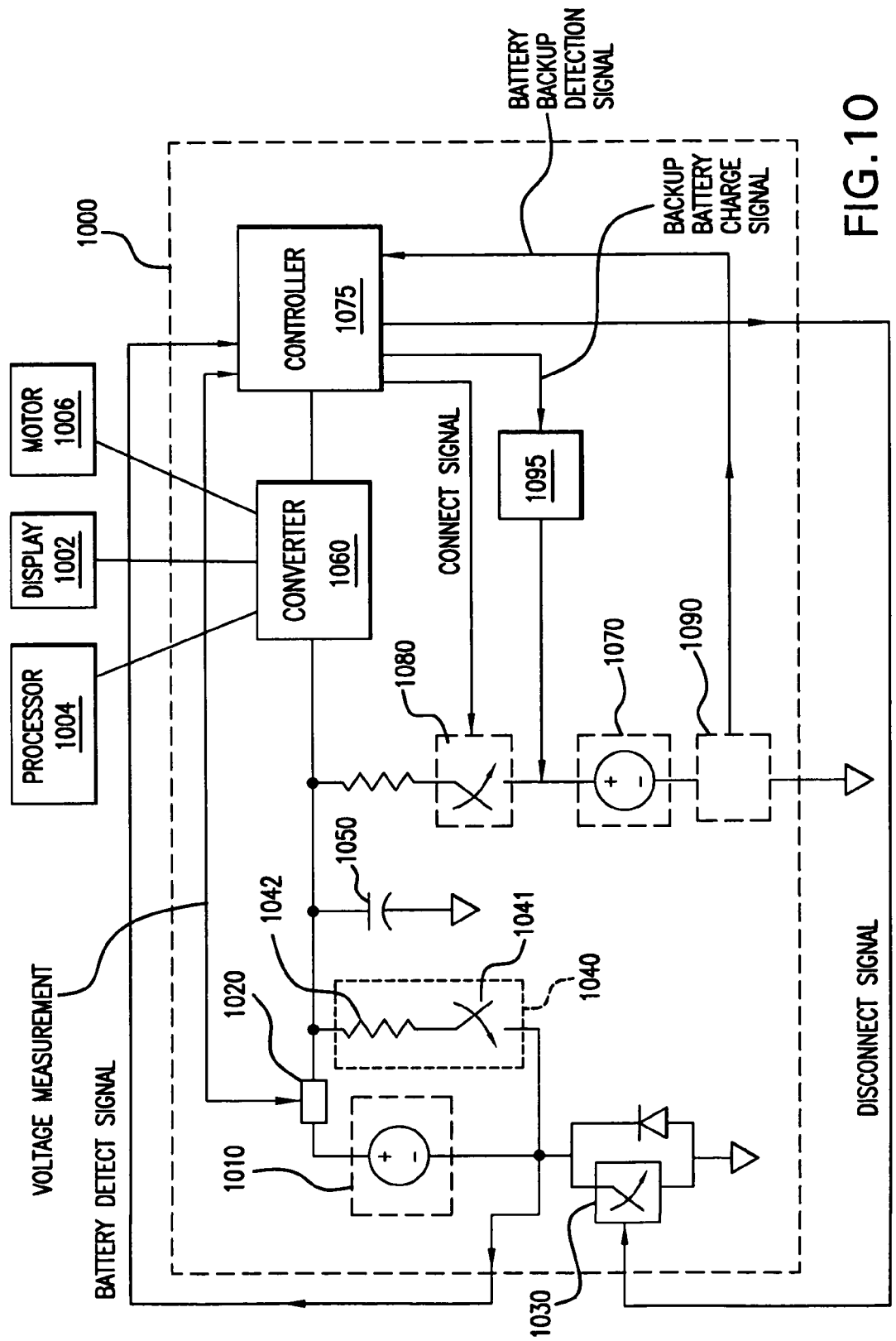
FIG. 10 illustrates a block diagram of a powering subsystem for a portable electronic device according to an embodiment of the present invention.

FIG. 10 illustrates a block diagram of a powering subsystem for a portable electronic device according to an embodiment of the present invention. The powering subsystem 1000 provides full functional power to the portable electronic device whether the main battery is providing the power or the backup battery is providing the power. This is unlike other powering subsystems for devices utilizing batteries where a backup battery only provides power to support a run-time clock and/or limited functionality for the portable electronic device. In an embodiment of the invention illustrated in FIG. 10, the powering circuit includes a main battery 1010, a main battery voltage measurement circuit 1020, a main battery connection circuit 1030, a main battery detection circuit 1040, a capacitor 1050, a voltage converter 1060, a backup battery 1070, a controller 1075, a backup battery connection circuit 1080, a backup battery monitoring circuit 1090, and a charging circuit 1095.

As the portable electronic device is utilized, the main battery 1010 is being drained because it is supplying the voltage and power for the portable electronic device. A main battery detection circuit 1040 monitors whether a main battery 1010 is installed in the portable electronic device. If the main battery is installed within the portable electronic device, the main battery detection circuit 1040 transmits a signal to the controller 1075 identifying that the main battery 1010 is installed. In an embodiment of the invention, a switch 1041 may be opened on a periodic basis, and a voltage may be measured across a resistor 1042 to verify that a voltage is being supplied by the main removable battery 1010. If a voltage is detected, the main battery detection signal is transmitted to the controller 1075.

Under certain operating conditions, if the main battery 1010 is determined to be installed, the controller 1075 transmits a signal request to the main battery voltage measurement circuit 1020 to obtain a voltage reading of the voltage supplied by the main battery 1010. Under certain other operating conditions, the controller 1075 may wait to receive a voltage level reading from the main battery voltage measurement circuit 1020. In an embodiment of the invention, the main battery voltage measurement circuit 1020 is measuring the voltage across the super capacitor (supercap) 1050. In an embodiment of the invention, the main battery voltage measurement circuit 1020 is measuring the voltage supplied by the main battery 1010.

The controller 1075, after receipt of the voltage level of the main battery 1010, compares the received voltage against a low voltage threshold level previously stored in the controller 1075. In an embodiment of the invention, the low voltage threshold is 0.8 volts. Illustratively, the low voltage threshold may be any voltage less than 1.0 volt, such as 0.5, 0.6, 0.72, or 0.93 volts. The low voltage threshold may be other voltages also. This is a decrease from previous low voltage thresholds for batteries, which ranged from 1.08 to 1.16 and allows more of the energy of the battery to be utilized for powering the portable electronic device. This results in the portable electric device being able to utilize a larger percentage of the battery energy, e.g., greater than 95% of the battery energy. This allows the user of the portable electronic device to spend less on batteries and also have a predictable time that the backup battery provides power to the portable electronic device.

Under normal operation of a portable electronic device, the main battery 1010 charges up the capacitor 1050. The capacitor 1050 supplies a voltage to the voltage converter 1060. The main battery 1010 cannot directly provide the power to the components of the portable electronic device, e.g., processors, controllers, or motors, because of the fluctuating characteristics of battery supplied voltage. The voltage converter 1060 steps up the voltage to a larger value and provides a plurality of voltages to other systems and components of the portable electronic device. For example, as illustrated in FIG. 10, the voltage converter 1060 provides a voltage to the controller 1075. In addition, the voltage converter 1060 provides voltages to a processor (e.g., like a processor utilized to perform calculations), a display system (for driving a display of the portable electronic device, and a motor (for driving mechanical systems within the portable electronic device). Illustratively, the voltage converter 1060 may receive an input of 0.8 to 2 volts, may step up or boost this voltage and may supply, for example, 3.0 volts, 3.3 volts, and 5.0 volts to the controller 1075 and other systems within the portable electronic device. In an embodiment of the invention, the portable electronic device is an insulin infusion pump. When the portable electronic device is an insulin pump, the other systems being provided voltage (or power) from the voltage converter 1060 are a display subsystem 1002 for driving a display of the infusion pump, a calculation processor 1004 for calculating a delivery amount of insulin based on input from a user of the infusion pump, and a motor 1006, for actually driving the delivery of the insulin from the infusion pump to the subject user.

After the main battery 1010 has been inserted, the controller 1075 receives an operating voltage from the voltage converter 1060 under normal operation. The controller 1075 may also transmit a signal to charge the backup battery 1070. In an embodiment of the invention, the controller 1075 transmits the signal to a charging circuit 1095 which in turn transmits a charging voltage to the backup battery 1070. This allow a backup battery 1070 to indirectly receive a charge voltage from the main battery 1010 to receive its power. Under certain operating conditions, the controller 1075 may determine the main battery 1010 has enough voltage to operate, but does not have enough voltage to charge the backup battery 1070. In this embodiment of the invention, the controller 1075 may issue an error message to the user indicating that there is not enough power in the main battery to charge the backup battery and therefore the backup battery is not being charged.

If the controller 1075 determines that the voltage level reading from the main battery 1010 (measured by the main battery voltage measurement circuit 1020) is drained below the low battery threshold voltage, the controller 1075 transmits a disconnect signal to the main battery connection circuit 1030 to disconnect the main battery from the powering circuit 1000. In an embodiment of the invention, the controller 1075 transmits a signal to a main battery connection circuit 1030 to uncouple the main battery 1010 from ground, which disconnects the main battery 1010 from providing power to the capacitor 1050 (and thus the power converter 1060 and microcontroller 1075). This does not disconnect power to the portable electronic device because the capacitor 1050 is stored with energy which is utilized and supplied to the converter 1060. Under certain operating conditions, this is also true when switching from backup battery power to main battery power.

In an embodiment of the invention, the controller 1075 transmits a connection signal to the backup battery connection circuit 1080 to make the backup battery 1070 the power supply for the power subsystem 1000 of the portable electronic device. In an embodiment of the invention, the controller 1075 transmits the backup battery connection signal to a switch 1080 that couples the backup battery 1070 to the capacitor 1050 (e.g., super capacitor) to charge the capacitor 1050. After the backup battery charges up the capacitor 1050, the capacitor 1050 provides a voltage to the converter 1060 which in turn provides operating voltages to the controller or processor 1075. The converter 1060 may also provide power to other devices such as a processor 1002, display system 1004, and motor 1006. The backup battery 1070 continues powering the subsystems of the portable electronic device for a minimum established period of time, e.g., 24, 36, or 48 hours, without a user of the portable electronic device worrying that the portable electronic device may fail. The backup battery 1070 may provide power for more than the minimum established period of time because the battery life is dependent upon the usage of the portable electronic device.

In an embodiment of the invention, the controller 1075 monitors the charge or voltage level of backup battery 1070 by measuring the voltage of the backup battery 1070. In an embodiment of the invention, a backup battery voltage detection circuit 1090 measures the voltage level of the backup battery 1070 and transmits a voltage level signal to the controller 1075. The controller 1075 receives the backup battery voltage level and compares it to a backup battery low threshold voltage. If the backup battery voltage level is below the backup battery low threshold voltage, the controller 1075 may transmit a message to a user that it is shutting down the portable electronic device or risk operational failure of the portable electronic device. This occurs only if a new main battery 1010 has not been inserted after the portable electronic device switched to being powered by the backup battery.

If the new or recharged main battery 1010 is inserted into the powering subsystem 1000, the main battery detection circuit 1040 determines that the new or recharged main battery 1010 has been placed into the powering subsystem 1000. If the main battery detection circuit 1040 detects the new main or recharged main battery 1010, a battery detection signal is transmitted to the controller 1075. The controller 1075 receives the battery detection signal and transmits the connection signal to the main battery connection circuit 1030 to place the main battery 1010 in parallel with the super capacitor 1050 to provide functional power to the portable electronic device (through the power converter 1060). The controller 1075 also transmits a backup battery connection signal to disconnect the backup battery 1070 from charging up the super capacitor 1050. In other words, the backup battery 1070 is no longer providing the power for the portable electronic device. After the backup battery 1070 has been disconnected from providing power to the super capacitor 1050, the controller 1075 also charges up the backup battery 1070, either directly or through the backup battery charging circuit 1095.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of providing backup power to a portable electronic device having a primary battery and a backup battery, the method comprising:
    monitoring a battery level of the primary battery of the portable electronic device;
    generating a first signal to cause the primary battery to be disconnected if the battery level of the primary battery is less than a low battery threshold voltage; and
    generating a second signal to cause the backup battery of the portable electronic device to provide power for the portable electronic device, wherein the backup battery is configured to be charged by the primary battery and provides power for operating the portable electronic device with full feature functionality for a period of at least 24 hours.

2. The method of claim 1, wherein the generation of the first signal and the second signal occur substantially simultaneously.

3. The method of claim 1, wherein the low battery threshold voltage is less than 1.0 volt.

4. The method of claim 1, wherein the low battery threshold voltage is less than 0.8 volts.

5. The method of claim 1, wherein the battery level and the low battery threshold are both values of a current supplied by the primary battery.

6. The method of claim 1, wherein the portable electronic device is an insulin pump.

7. A method of providing power to a portable electronic device having a main battery and a backup battery, the method comprising:
    detecting whether the main battery has been inserted into the portable electronic device and transmitting a detection signal to a controller if the main battery is detected;
    coupling a voltage from the main battery to a power converter after the main battery has been detected;
    providing an operating voltage to a controller, the operating voltage being provided from the power converter after the power converter receives the voltage;
    upon detection of the main battery, automatically charging the backup battery of the portable electronic device utilizing a signal transmitted from the controller, so as to charge the backup battery by the main battery;
    monitoring a battery level of the backup battery to determine if the backup battery has reached a charging level; and
    disabling the charging of the backup battery if the charging level of the backup battery has been exceeded.

8. The method of claim 7, further including monitoring a battery level of the main battery to determine if the main battery has been drained below a main battery low threshold voltage.

9. The method of claim 8, further including transmitting a disconnection signal to disconnect the main battery from coupling the voltage to the power converter if the main battery has been drained below the main battery low threshold voltage.

10. The method of claim 9, further including transmitting a connection signal to connect the backup battery to provide power to the power converter if the main battery has been drained below the threshold main battery level.

11. The method of claim 10, wherein a capacitor is coupled between the main battery and the power converter, the capacitor receives the voltage from the main battery, and provides the voltage to the power converter.

12. The method of claim 10, further including monitoring the portable electronic device to determine if a sufficiently charged main battery has been inserted into the portable electronic device and transmitting a detection signal to the controller if the sufficiently charged main battery has been installed.

13. The method of claim 12, further including transmitting a main battery connection signal to connect the main battery if the sufficiently charged main battery has been inserted into the portable electronic device and transmitting a backup battery connection signal to disconnect the backup battery from providing power to the power converter.

14. The method of claim 13, further including the controller checking a level of the backup battery to determine a charging level of the backup battery and to charge the backup battery if the charging level is below an acceptable threshold.

15. The method of claim 7, wherein the portable electronic device is an insulin pump.

16. A program code storage device, comprising:
program code storage device; and
machine-readable program code, stored on the program code storage device, the machine-readable program code having instructions, which when executed, cause a controller for a portable electronic device having a main battery and a backup battery to:
receive a battery detect signal from the main battery of the portable electronic device;
receive a main battery voltage reading;
compare the main battery voltage reading against a main battery low voltage threshold;
if the main battery voltage reading is less than or equal to the main battery low voltage threshold, transmit a main battery disconnect signal to a switching device to disconnect the main battery from providing power to the controller; and
transmit a backup battery connect signal to a switching device to connect the backup battery of the portable electronic device to provide power to the controller to allow full feature functionality for a period of at least 24 hours, said backup battery having been charged by the main battery of the portable electronic device.

17. The program code storage device of claim 16, including instructions, which when executed, cause the controller to transmit a message to a display of the portable electronic device indicating a minimum time for which the backup battery can provide power for the portable electronic device.

18. The program code storage device of claim 16, including instructions, which when executed, transmit a request for the main battery voltage reading to a main battery detection circuit if the battery detect signal is received.

19. A program code storage device, comprising:
program code storage media; and
machine-readable program code, stored on the program code storage media, the machine-readable program code including instructions, which when executed cause a controller for a portable electronic device having a main battery and a backup battery to:
receive a main battery detection signal indicating that the main battery of the portable electronic device is present within a powering circuit of the portable electronic device;
receive an operating level of the backup battery of the portable electronic device;
upon receipt of the main battery detection signal, automatically transmit a signal to a backup battery charging circuit to charge the backup battery by the main battery if the operating level is below a backup battery charging threshold;
receive a charging level of the backup battery; and
stop transmitting the signal to the charging circuit if the charging level of the backup battery is above the charging threshold.

20. The program code storage device of claim 19, including instructions, which when executed cause the controller to receive a main battery voltage reading and compare the main battery voltage reading against a main battery threshold voltage.

21. The program code storage device of claim 20, including instructions, which when executed cause the controller to transmit a main battery disconnect signal to cause the main battery to cease providing power to the microcontroller and to transmit a backup battery connect signal to cause the backup battery to provide power to the microcontroller.

22. A powering subassembly for a portable insulin pump comprising:
a main battery to provide a main voltage to the insulin pump;
a converter to receive the main voltage and to increase the main voltage to at least one operating voltage;
a backup battery configured to be charged by the main battery and to provide a backup voltage to the insulin pump to allow the insulin pump to operate with full feature functionality for a period of at least 24 hours; and
a controller to receive the operating voltage from the converter, to monitor a voltage level of the main battery, to compare the monitored voltage level of the main battery to a main battery low voltage threshold, to transmit a disconnect signal to prevent the main battery from providing the main voltage to the converter if the monitored voltage level is less than or equal to the main battery low voltage threshold, to transmit a connection signal to the backup battery to cause the backup battery to provide a backup voltage to the converter, and to receive an operating level of the backup battery and automatically transmit a signal to a charging device to charge the backup battery by the main battery if the operating level of the backup battery is below a charging threshold.

23. The powering subassembly according to claim 22, further including a switching device to uncouple the main battery from a reference ground after receiving the disconnect signal.

24. The powering subassembly according to claim 22, wherein a capacitor is coupled between the main battery and the converter, the capacitor is charged up by the main battery and the capacitor provides a smoother main voltage to the converter.

25. The powering subassembly according to claim 22, wherein the controller monitors a charging level of the backup battery and discontinues transmission of the signal to the charging device if the charging level of the backup battery is above the charging threshold.

26. The powering subassembly of claim 22, wherein the main battery low voltage threshold is less than 1.0 volts.

27. The power subassembly of claim 22, wherein the main battery low voltage threshold is less than 0.8 volts.

28. The powering subassembly of claim 22, wherein rechargeable, lithium, or alkaline batteries can be utilized by the insulin pump.

29. The powering subassembly according to claim 22, wherein at least 95% of the main battery energy is utilized before the main battery reaches a low voltage threshold.

30. The powering subassembly according to claim 22, wherein the converter provides other operating voltages to a pump, a display, and a second processor, the second processor not being the controller.

31. A portable insulin pump, comprising:
- a display to provide messages to a user; and
- a powering subassembly, the powering subassembly including:
- a main battery to provide a main voltage to the portable insulin pump;
- a backup battery configured to be charged by the main battery and to provide a backup voltage to the portable insulin pump to allow the insulin pump to operate with full feature functionality for a period of at least 24 hours;
- a capacitor, coupled to one of the main battery and the backup battery, and capable of being coupled to both the main battery and the backup battery, to receive either the main voltage or the backup voltage, and to transfer the received voltage;
- a converter to receive the received voltage from the capacitor and to generate at least one operating voltage; and
- a controller to receive the at least one operating voltage from the converter, to monitor the main voltage of the main battery, to compare the monitored level of the main battery to a main battery low voltage threshold, to transmit a disconnect signal to prevent the main voltage from the main battery from being coupled to the capacitor if the monitored level of the main battery is less than or equal to the main battery low voltage threshold, and to automatically transmit a signal to a charging device to charge the backup battery by the main battery if the backup voltage of the backup battery is below a charging threshold.

32. The insulin pump of claim 31, wherein the controller further transmits a connect signal to couple the backup voltage from the backup battery to the capacitor if the monitored level of the main battery is less than or equal to the main battery low voltage threshold.

33. The insulin pump of claim 32, wherein the converter provides an operating voltage for the display.

34. The insulin pump of claim 32, wherein the main battery can be a removable rechargeable battery which can be recharged by household current.

35. The insulin pump of claim 31, wherein the main battery low voltage threshold is less than 1.0 volts.

36. The insulin pump of claim 31, wherein the main battery low voltage threshold is less than 0.8 volts.

37. The insulin pump of claim 31, wherein at least 95% of the main battery energy is utilized before the main battery reaches a low voltage threshold.

* * * * *